(12) United States Patent
Martin et al.

(10) Patent No.: US 7,378,402 B2
(45) Date of Patent: *May 27, 2008

(54) ANTI-VIRAL NUCLEOSIDES

(75) Inventors: Joseph Armstrong Martin, Hertfordshire (GB); Keshab Sarma, Sunnyvale, CA (US); David Bernard Smith, San Mateo, CA (US); Mark Smith, San Francisco, CA (US)

(73) Assignee: Roche Palo Alto LLC, Palo Alto, CA (US)

( * ) Notice: Subject to any disclaimer, the term of this patent is extended or adjusted under 35 U.S.C. 154(b) by 231 days.

This patent is subject to a terminal disclaimer.

(21) Appl. No.: 11/208,510

(22) Filed: Aug. 22, 2005

(65) Prior Publication Data

US 2006/0040890 A1 Feb. 23, 2006

Related U.S. Application Data

(60) Provisional application No. 60/603,778, filed on Aug. 23, 2004.

(51) Int. Cl.
C07H 19/00 (2006.01)
C07H 19/06 (2006.01)
A01N 43/04 (2006.01)
A61K 31/70 (2006.01)

(52) U.S. Cl. ............... 514/49; 536/28.1; 536/28.4; 536/28.5; 536/28.51

(58) Field of Classification Search ............... None
See application file for complete search history.

(56) References Cited

U.S. PATENT DOCUMENTS

| | | | |
|---|---|---|---|
| 5,034,518 A | 7/1991 | Montgomery et al. | |
| 5,246,924 A | 9/1993 | Fox et al. | |
| 5,587,362 A | 12/1996 | Chu et al. | |
| 6,348,587 B1 | 2/2002 | Schinazi et al. | |
| 6,784,166 B2 * | 8/2004 | Devos et al. | 514/47 |
| 6,846,810 B2 * | 1/2005 | Martin et al. | 514/49 |
| 6,864,244 B2 * | 3/2005 | Connolly et al. | 514/49 |

FOREIGN PATENT DOCUMENTS

| | | |
|---|---|---|
| EP | 0 292 023 A2 | 5/1988 |
| EP | 0 352 248 A1 | 1/1990 |
| EP | 0 357 571 B1 | 4/1996 |
| WO | WO 00/69876 A1 | 11/2000 |
| WO | WO 00/69877 A1 | 11/2000 |
| WO | WO 02/100415 A2 | 12/2002 |
| WO | WO 03/026589 A2 | 4/2003 |
| WO | WO 03/026675 A1 | 4/2003 |
| WO | WO 03/039523 A2 | 5/2003 |

OTHER PUBLICATIONS

Carroll, S. S., "Inhibition of Hepatitis C Virus RNA Replication by 2'-Modified Nucleoside Analogs", *Journal of Biological Chemistry*, 2003, 278(14):11979-11984.

Jeon, G. S., et al., "New Isomeric Analogues of Anti-HIV Active Azidonucleosides", *Tetrahedron*, 1996, 52(39):12643-50.

Jin, Y., et al, "Synthesis and Antiviral Activity of Fluoro Sugar Nucleosides 1: Studies on 4"-Azido-2'-Deoxy-2'-Fluoro-Arabinofuranosyl Nucleosides", *Arch. Pharm Res.*, 1995, 18(5):364:365.

Khogo, Satoru, et al., "Synthesis of 4'-C-ethylnyl-β-arabino- and 4'-C-ethynyl-2'-deoxy-β-D-ribopentofuranosyl pyrimidines, and their biological evaluation", *Bioscience, Biotechnology, and Biochemistry* (1999), 63(6), 1146-1149.

Khogo, Satoru, et al., "Synthesis of 4'-substituted nucleosides and t heir biological evaluation", *Nucleic Acids Symposium Series* (1999), 42 (*Twentysixth Symposium on Nucleic Acids Chemistry, 1999*), 127-128.

Kitano, K., et al., "Synthesis of 4'-C-Fluoromethylnucleosides as Potential Antineoplastic Agents", *Tetrahedron*, 1997, 53(39):13315-13322.

Kodama, E., et al., "4'-Ethynyl Nucleoside Analogs: Potent Inhibitors of Multidrug-Resistant Human Immunodeficiency Virus Variants in Vitro", *Antimocrobial Agents and Chemotherapy*, 2001, 45(5):1539-1546.

Maag, H., et al, "Synthesis and Anti-HIV Activity of 4'-Azido and 4'-Methoxynucleosides", *J. Med Chem*, 1992, 35:1440:1451.

Ohrui, H., "Syntheses of 4'-C-Ethynyl-β-D-arabino- and 4'-C-Ethynyl-2'-deoxy-β- D-ribo-pentofuranosylpyrimidines and — purines and Evaluation of Their Anti-HIV Activity", *J. Med. Chem.*, 2000, 43:4516-4525.

Waga, T., "Synthesis and Biological Evaluation of 4'-C-Methyl Nucleosides", *Nucleosides and Nucleotides*, 1996, 15(1-3):287-304.

Wu. J.Z., et al., "Targeting NS5B RNA-Dependent RNA Polymerase for Anti-HCV Chemotherapy", *Curr. Drug Targ. Inf. Dis.*, 2003, 3(3):207-219.

Yamaguchi, Toyofumi, et al., "Antileukemic activities and mechanism of action of 2'-deoxy-4'-methylcytidine and related nucleosides", *Nucleosides & Nucleotides* (1977), 16(7-9), 1347-1350.

* cited by examiner

*Primary Examiner*—Shaojia Anna Jiang
*Assistant Examiner*—Traviss C. McIntosh, III
(74) *Attorney, Agent, or Firm*—Brian L. Buckwalter

(57) ABSTRACT

4-Amino-1-((2R,3S,4S,5R)-5-azido-3,4-dihydroxy-5-hydroxymethyl-tetrahydro-furan-2-yl)-1H-pyrimidin-2-one (I:$R^1=R^2=R^3=R^4=H$) and prodrugs thereof are hepatitis C(HCV) polymerase inhibitors. Also disclosed are compositions and methods for inhibiting HCV and treating HCV-mediated diseases, processes for making the compounds and synthetic intermediates employed in the process.

23 Claims, No Drawings

ANTI-VIRAL NUCLEOSIDES

REFERENCE TO PRIOR APPLICATIONS

This application claims the benefit of priority to U.S. Ser. No. 60/603,778 filed Aug. 23, 2004 which is hereby incorporated by reference in its entirety.

FIELD OF THE INVENTION

The present invention provides nucleoside compounds and certain derivatives thereof which are inhibitors of RNA-dependent RNA viral polymerase. These compounds are inhibitors of RNA-dependent RNA viral replication and are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

The invention relates to nucleoside inhibitors of HCV replicon RNA replication. In particular, the invention is concerned with the use of pyrimidine nucleoside compounds as inhibitors of subgenomic HCV RNA replication and pharmaceutical compositions containing such compounds.

Hepatitis C virus is the leading cause of chronic liver disease throughout the world. (Boyer, N. et al. *J. Hepatol.* 2000 32:98-112). Patients infected with HCV are at risk of developing cirrhosis of the liver and subsequent hepatocellular carcinoma and hence HCV is the major indication for liver transplantation.

HCV has been classified as a member of the virus family Flaviviridae that includes the genera flaviviruses, pestiviruses, and hapaceiviruses which includes hepatitis C viruses (Rice, C. M., *Flaviviridae: The viruses and their replication*, in: *Fields Virology*, Editors: Fields, B. N., Knipe, D. M., and Howley, P. M., Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a 5'-untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forns and J. Bukh, *Clinics in Liver Disease* 1999 3:693-716; J. Bukh et al., *Semin. Liv. Dis.* 1995 15:41-63).

Unfortunately Type 1 infections are more resistant to therapy than either type 2 or 3 genotypes (N. N. Zein, *Clin. Microbiol. Rev.,* 2000 13:223-235).

Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. These proteases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown. It is believed that most of the non-structural proteins encoded by the HCV RNA genome are involved in RNA replication Currently there are a limited number of approved therapies are currently available for the treatment of HCV infection. New and existing therapeutic approaches to treating HCV and inhibition of HCV NS5B polymerase have been reviewed: R. G. Gish, *Sem. Liver. Dis.,* 1999 19:5; Di Besceglie, A. M. and Bacon, B. R., *Scientific American,* October: 1999 80-85; G. Lake-Bakaar, Current and Future Therapy for Chronic Hepatitis C Virus Liver Disease, *Curr. Drug Targ. Infect Dis.* 2003 3(3):247-253; P. Hoffmann et al., Recent patents on experimental therapy for hepatitis C virus infection (1999-2002), *Exp. Opin. Ther. Patents* 2003 13(11):1707-1723; M. P. Walker et al., Promising Candidates for the treatment of chronic hepatitis C, *Exp. Opin. investing. Drugs* 2003 12(8):1269-1280; S.-L. Tan et al., Hepatitis C Therapeutics: Current Status and Emerging Strategies, *Nature Rev. Drug Discov.* 2002 1:867-881.

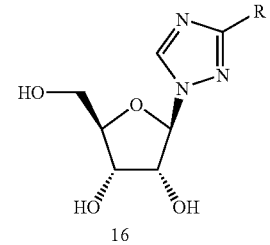

1a: R = C(═O)NH$_2$
1b: R = C(═NH$^+$)NH$_2$

Ribavirin (1a; 1-((2R,3R,4S,5R)-3,4-Dihydroxy-5-hydroxymethyl-tetrahydro-furan-2-yl)-1H-[1,2,4]triazole-3-carboxylic acid amide; Virazole) is a synthetic, non-interferon-inducing, broad spectrum antiviral nucleoside analog. Ribavirin has in vitro activity against several DNA and RNA viruses including Flaviviridae (Gary L. Davis, *Gastroenterology* 2000 118:S104-S114). In monotherapy ribavirin reduces serum amino transferase levels to normal in 40% of patients, but it does not lower serum levels of HCV-RNA. Ribavirin also exhibits significant toxicity and is known to induce anemia. Viramidine 1b is a prodrug converted to 1a in hepatocytes Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon β, type 2 includes interferon γ. Type 1 interferons is produced mainly by infected cells and protects neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (L.-B. Davis, supra)

One limitation of early IFN therapy was rapid clearance of the protein from the blood. Chemical derivatization of IFN with polyethyleneglycol (PEG) has resulted in proteins with substantially improved pharmacokinetic properties. PEGASYS® is a conjugate interferon α-2a and a 40 kD branched mono-methoxy PEG and PEG-INTRON® is a conjugate of interferon α-2b and a 12 kD mono-methoxy PEG. (B. A. Luxon et al., *Clin. Therap.* 2002 24(9):13631383; A. Kozlowski and J. M. Harris, *J. Control. Release*, 2001 72:217-224).

Combination therapy of HCV with ribavirin and interferon-α currently represent the optimal therapy. Combining ribavirin and PEG-IFN (infra) results in a sustained viral response in 54-56% of patients. The SVR approaches 80% for type 2 and 3 HCV. (Walker, supra) Unfortunately, the combination also produces side effects which pose clinical challenges. Depression, flu-like symptoms and skin reactions are associated with subcutaneous IFN-α and hemolytic anemia is associated with sustained treatment with ribavirin.

A number of potential molecular targets for drug development as anti-HCV therapeutics have now been identified including, but not limited to, the NS2-NS3 autoprotease, the N3 protease, the N3 helicase and the NS5B polymerase. The RNA-dependent RNA polymerase is absolutely essential for replication of the single-stranded, positive sense, RNA genome. This enzyme has elicited significant interest among medicinal chemists.

Nucleoside inhibitors can act either as a chain terminator or as a competitive inhibitor which interferes with nucleotide binding to the polymerase. To function as a chain terminator the nucleoside analog must be taken up be the cell and converted in vivo to a triphosphate to compete for the polymerase nucleotide binding site. This conversion to the triphosphate is commonly mediated by cellular kinases which imparts additional structural requirements on a potential nucleoside polymerase inhibitor. In addition this limits the direct evaluation of nucleosides as inhibitors of HCV replication to cell-based assays capable of in situ phosphorylation.

In WO 01 90121 published Nov. 29, 2001, J.-P. Sommadossi and P. Lacolla disclose and exemplify the anti-HCV polymerase activity of 1'-alkyl- and 2'-alkyl nucleosides of formulae 2 and 3. In WO 01/92282, published Dec. 6, 2001, J.-P. Sommadossi and P. Lacolla disclose and exemplify treating Flaviviruses and Pestiviruses with 1'-alkyl- and 2'-alkyl nucleosides of formulae 2 and 3. In WO 03/026675 published Apr. 3, 2003, G. Gosselin discloses 4'-alkyl nucleosides 4 for treating Flaviviruses and Pestiviruses. In WO2004003000 published Jan. 8, 2004, J.-P. Sommadossi et al. disclose 2'- and 3' prodrugs of 1'-, 2'-, 3'- and 4'-substituted β-D and β-L nucleosides. Idenix has reported clinical trials for a related compound NM283 which is believed to be the valine ester 5 of the cytidine analog 2 (B=cytosine).

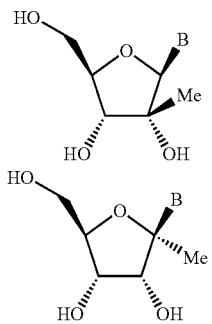

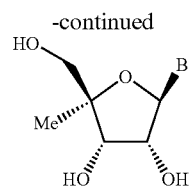

-continued

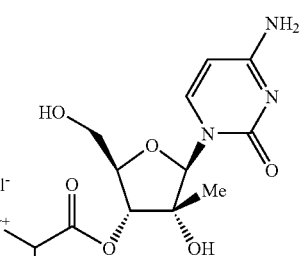

B = adenine, thymidine, uracil, cytidine, guanine and hypoxanthine

In WO02/05787 published Jul. 25, 2002, S. S. Carroll et al. disclose related 2α-methyl and 2β-methylribose derivatives wherein the base is an optionally substituted 7H-pyrrolo[2,3-d]pyrimidine radical 6. The same application discloses one example of a 3β-methyl nucleoside. S. S. Carroll et al. (*J. Biol. Chem.* 2003 278(14):11979-11984) disclose inhibition of HCV polymerase by 2'-O-methylcytidine (6a).

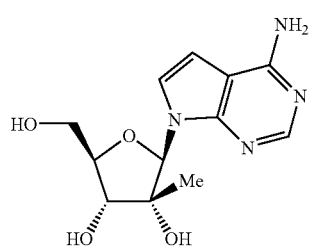

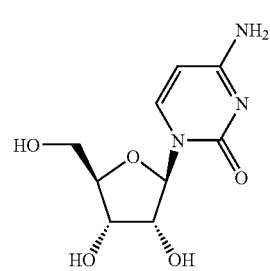

Modification of nucleosides by substitution at the 4'-position has been less prevalent, most like due to the added synthetic challenges associated with their synthesis. Maag et al. (Anti-HIV Activity of 4'-Azido and 4'-Methoxynucleosides, *J. Med. Chem.* 1992 35:1440-1451) disclose the synthesis of 4'-azido-2-deoxyribonucleosides and 4-azido nucleosides. C. O'Yang, et al. (*Tetrahedron Lett.* 1992 33(1):37-40 and 33(1):41-44) disclose the synthesis 4'-cyano, 4'-hydroxymethyl- and 4'-formyl nucleoside compounds substituted nucleosides. These compounds were evaluated as anti-HIV compounds.

In WO02/100415 published Dec. 19, 2002 (US 2003/0236216 A1), R. R. Devos et al. disclose 4'-substituted nucleoside compounds that exhibit HCV activity. Four compounds explicitly identified include the 4'-azido compound, 7a, the 4'-ethynyl compound 7b, the 4'-ethoxy compound 7c and the 4'-acetyl compound 7d. Modifications to the ribose moiety exemplified include the 2'-deoxy 8a derivative, 3'-deoxy derivative 8b, the 3'-methoxy derivative 8e, the 3'-fluoro derivative 8c and the 2',2'-difluoro derivative 8d. In WO2004/046159 published Jun. 3, 2004 (US 2004121980), J. A. Martin et al. disclose prodrugs of 7a useful for treating HCV-mediated diseases. Both US applications are hereby incorporated by reference in their entirety. While compounds with the arabinose configuration fall within genus, these compounds are not among specifically disclosed, exemplified, or included in the preferred list of nucleosides in the specification.

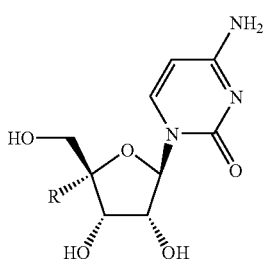

7a: R = N$_3$
7b: R = ethynyl
7c: R = OEt
7d: R = C(═O)Me

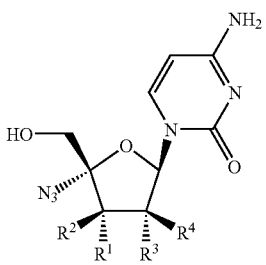

8a: R$^1$ = OH, R$^2$ = R$^3$ = R$^4$ = H
8b: R$^3$ = OH, R$^1$ = R$^2$ = R$^4$ = H
8c: R$^3$ = OH, R$^2$ = F, R$^1$ = R$^4$ = H
8d: R$^1$ = R$^2$ = H, R$^3$ = R$^4$ = F
8e: R$^1$ = OMe, R$^3$ = OH, R$^2$ = R$^4$ = H

U.S. application Ser. No. 10/167,106 filed Jun. 11, 2002 entitled "4'-Substituted Nucleoside Derivatives as Inhibitors of HCV RNA Replication", and U.S. application Ser. No. 10/717,260 file Nov. 19, 2003 disclose compounds related to the present invention. Both applications are incorporated herein in their entirety by reference.

Y.-H. Yun et al. (*Arch. Pharm. Res.* 1985 18(5):364-35) disclose the synthesis and antiviral activity of 4'-azido-2'-deoxy-2'-fluoro-arabinofuranosyl nucleosides (9: R=H, Me and Cl).

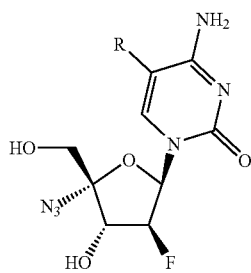

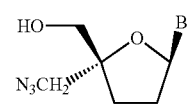

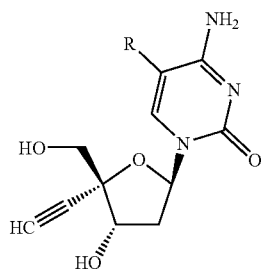

B = adenine, uracil, thymine

G. S. Jeon and V. Nair (*Tetrahedron* 1996 52(39): 12643-50) disclose the synthesis 4'-azidomethyl-2', 3'-deoxyribonucleosides 10 (B=adenine, thymine and uracil) as HIV reverse transcriptase inhibitors.

Several computational studies of 4'-azidonucleosides have been reported: D, Galisteo et al., *J. Mol. Struct.* 1996 384(1):25-33; J. Pepe et al., *Eur. J. Med. Chem.* 1996 32(10):775-786; E. Estrada et al., In silico studies toward the discovery of New Anti HIV Nucleoside, *J. Chem. Info. Comp. Sci.* 2002 42(5): 1194-1203;

I. Sugimoto et al. disclosed the synthesis and the HIV and H. simplex bioassay of 4'-ethynyl-2'-deoxycytidine (11) and other two-carbon substituents at the 4'-position (Nucleosides and Nucleotides. 183. Synthesis of 4' α-Branched Thymidines as a New Type of Antiviral Agent, *Bioorg Med. Chem. Lett.* 1999 9:385-88). T. Wada et al. (*Nucleosides & Nucleotides* 1996 15(1-3):287-304) disclose the synthesis and anti-HIV activity of 4'-C-methyl nucleosides.

In WO 01/32153 published May 10, 2001, R. Storer discloses methods of treating or preventing Flaviviridae viral infection by administering dioxolane analogs of nucleosides In WO02/18404 published Mar. 7, 2002, R. Devos et al. disclose novel and known purine and pyrimidine nucleoside derivatives and their use as inhibitors of subgenomic HCV replication and pharmaceutical compositions containing said nucleoside derivatives. The compounds disclosed consist of nucleosides with substituted purine and pyrimidine bases.

Several references have reported the synthesis and use of fluoro-nucleosides with the arabinose configuration for therapy of viral diseases. There have been several reports of 2-fluoro-β-D-arabinofuranosyl nucleosides that exhibit activity against hepatitis B and herpes. See, for example, U.S. Pat. No. 6,348,587 B1 (R. F. Schinazi et al.), U.S. Pat. No. 4,666,892 (Fox, et al.); U.S. Pat. No. 4,211,773 (Lopez, et al); Su, et al., Nucleosides. 136, Synthesis and Antiviral Effects of Several 1-(2-Deoxy-2-fluoro-β-D-arabinofuranosyl)-5-alkyluracils. Some Structure-Activity Relationships, *J. Med. Chem.* 1986 29:151-154; Borthwick, et al., Synthesis and Enzymatic Resolution of Carbocyclic 2'-Ara-fluoro-Guanosine: A Potent New Anti-Herpetic Agent, *J. Chem. Soc., Chem. Commun.* 1988; Wantanabe, et al., Synthesis and Anti-HIV Activity of 2'-"Up"-Fluoro Analogues of Active Anti-Aids Nucleosides 3'-Azido-3'-deoxythymidine (AZT) and 2',3'-dideoxycytidine (DDC), *J. Med. Chem.* 1990 33:2145-2150; Martin, et al., Synthesis and Antiviral Activity of Monofluoro and Difluoro Analogues of Pyrimidine Deoxyribonucleosides against Human Immunodeficiency Virus (HIV-1), *J. Med. Chem.* 1990 33:2137-2145; Sterzycki et al., Synthesis and Anti-HIV Activity of Several 2'-Fluoro-Containing Pyrimidine Nucleosides, *J. Med. Chem.* 1990; and Montgomery, et al., 9-(2-Deoxy-2-fluoro-β-D-arabinofuranosyl)guanine: A Metabolically Stable Cytotoxic Analogue of 2'-Deoxyguanosine. U.S. Pat. No. 5,246,924 discloses a method for treating a hepatitis infection that includes the administration of 1-(2'-deoxy-2'-fluoro-β-D-arabinofuranosyl)-3-ethyluracil). U.S. Pat. No. 5,034,518 discloses 2-fluoro-9-(2-deoxy-2-fluoro-β-D-arabinofuranosyl)adenine nucleosides which exhibit anticancer activity by altering the metabolism of adenine nucleosides by reducing the ability of the compound to serve as a substrate for adenosine. EPA 0 292 023 discloses that certain β-D-2'-fluoroarabinonucleosides are active against viral infections It has also been disclosed that L-FMAU (2'-fluoro-5-methyl-β-L-arabinofuranosyluracil) is a potent anti-HBV and anti-EBV agent. See Chu, et al., Use of 2'-Fluoro-5-methyl-β-L-arabinofuranosyluracil as a Novel Antiviral Agent for Hepatitis B Virus and Epstein-Barr Virus Antimicrobial Agents and Chemotherapy, 1995 39(4):979-98; Balakrishna, et al., Inhibition of Hepatitis B Virus by a Novel L-Nucleoside, 2'-Fluoro-5-Methyl-β-L-arabinofuranosyl Uracil, *Antimicrobial Agents and Chemotherapy,* 1996 40(2):380-356; U.S. Pat. Nos. 5,587,362; 5,567,688; and 5,565,438.

EPA Publication No. 0 352 248 discloses a broad genus of L-ribofuranosyl purine nucleosides for the treatment of HIV, herpes, and hepatitis. A similar specification is found in WO 88/09001, filed by Aktiebolaget Astra.

European Patent Application 0 357 571 discloses a broad group of β-D and α-D pyrimidine nucleosides for the treatment of AIDS which among the broad class generically includes nucleosides that can be substituted in the 2' or 3'-position with a fluorine group.

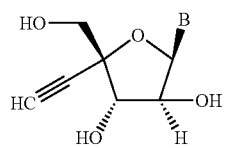

12a: B = cytosine
12b: B = thymine

H. Ohrui et al. (*Antimicrobial Agents and Chemother.* 2001 45(5):1539-1546; see also S. Koghgo et al., Tennen Yuki Kagobutsu Toronkai Koen Yoshishu 2000 42:835 (Chem. Abs. 2001:102156 anad H. Ohrui et al. WO2000069876 published Nov. 23, 2000) disclose the synthesis and anti-HIV activity of 4'-C-ethynyl-β-D-arabino- and 4'-C-ethynyl-2'-deoxy-β-D-ribo-pentofuranosyl pyrimidines and -purines. 4-Ethynyl-cytarabine (12a) exhibits good anti-HIV activity while the corresponding nucleoside wherein the base was thymine 12b was inactive. Several 4'-C-ethylnyl-2'-deoxy-β-D-ribo-pentofuranosyl pyrimidines and -purines were potent inhibitors of HIV reverse transcriptase (HIV-RT).

K. Kitano et al. (*Tetrahedron* 1997 53(39): 13315-13322) disclose the synthesis 4'-fluoromethyl 2-deoxy-D-erythro-, ribo- and arabino-pentofuranosyl cytosines and anti-neoplastic activity.

Intensive effort has focused on the identification of non-nucleoside inhibitors of HCV NS5B polymerase. The results of these efforts have been reviewed (J. Z. Chen and Z. Hong, Targeting NS5B RNA-Dependent RNA Polymerase for Anti-HCV Chemotherapy, Curr. Drug Targ. *Inf Dis.* 2003 3(3):207-219). The non-nucleoside inhibitors are not related to the present invention.

The object of the present invention is to provide new compounds, methods and compositions for the treatment of a host infected with hepatitis C virus.

SUMMARY OF THE INVENTION

The present invention is directed toward novel compounds that inhibit HCV polymerase, methods for inhibiting HCV polymerase and for treating a disorder mediated by HCV with said compounds and pharmaceutical compositions containing said compound which compound possesses a structure according to formula I

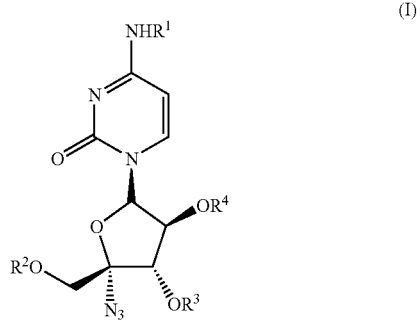

wherein:

$R^1$, $R^2$, $R^3$ and $R^4$ are independently selected from the group consisting of hydrogen, $COR^5$, $C(=O)OR^5$, $C(=O)SR^5$, $C(=O)NHR^5$ and $COCH(R^6)NHR^7$;

$R^5$ is independently selected from the group consisting of $C_{1-18}$ unbranched or branched alkyl, $C_{1-18}$ unbranched or branched alkenyl, $C_{1-18}$ unbranched or branched alkynyl, $C_{1-18}$ lower haloalkyl, $C_{3-8}$ cycloalkyl, $C_{3-8}$ cycloalkyl-$C_{1-3}$ alkyl, phenyl optionally substituted with one to three substituents independently selected from the group consisting of halogen, lower alkyl, lower alkoxy, lower thioalkyl, lower alkyl sulfinyl, lower alkyl sulfonyl, nitro and cyano, $CH_2Ph$ wherein in phenyl ring is optionally substituted as described above, and $CH_2OPh$ wherein in phenyl ring is optionally substituted as described above;

$R^6$ is independently selected from the group consisting of the side chains of naturally occurring amino acids and $C_{1-5}$ unbranched or branched alkyl;

$R^7$ is selected from the group consisting of hydrogen and $R^5OCO$; or, $R^6$ and $R^7$ taken together are $(CH_2)_3$; and, hydrates, solvates, clathrates and acid addition salts thereof.

DETAILED DESCRIPTION OF THE INVENTION

In one embodiment of the present invention there is provided a compound according to formula I wherein $R^1$, $R^2$, $R^3$, $R^4$, $R^5$, $R^6$ and $R^7$ are as defined herein above.

In another embodiment of the present invention there is provided a compound according to formula I wherein $R^1$, $R^2$, $R^3$, and $R^4$ each are independently $COR^5$, $C(=O)OR^5$, $C(=O)SR^5$; and, in each incidence, $R^5$, $R^6$ and $R^7$ are as defined hereinabove.

In another embodiment of the present invention there is provided a compound according to formula I wherein $R^1$, $R^2$, $R^3$, and $R^4$ each are independently $COR^5$, $C(=O)OR^5$, $C(=O)SR^5$; and $R^5$ in each instance is independently selected from the group consisting of unbranched or branched $C_{1-18}$ alkyl, optionally substituted phenyl and $CH_2OPh$.

In another embodiment of the present invention there is provided a compound according to formula I wherein $R^1$ is hydrogen; $R^2$, $R^3$, and $R^4$ each are independently $COR^5$, $C(=O)OR^5$, $C(=O)SR^5$ or $COCH(R^6)NHR^7$; and, in each incidence, $R^5$, $R^6$ and $R^7$ are as defined hereinabove.

In another embodiment of the present invention there is provided a compound according to formula I wherein $R^1$ is hydrogen; $R^2$, $R^3$, and $R^4$ are $COR^5$; and, each $R^5$ is independently selected from the group defined hereinabove.

In another embodiment of the present invention there is provided a compound according to formula I wherein $R^1$ is hydrogen; $R^2$, $R^3$, and $R^4$ are $COR^5$; and, $R^5$ is independently selected from the group consisting of is $C_{1-18}$ unbranched or branched alkyl, $C_{3-8}$ cycloalkyl and optionally substituted phenyl.

In another embodiment of the present invention there is provided a compound according to formula I wherein $R^1$, $R^3$, and $R^4$ are hydrogen; $R^2$ is $COR^5$, $C(=O)OR^5$, $C(=O)SR^5$ or $COCH(R^6)NHR^7$; and, $R^5$, $R^6$ and $R^7$ are as defined hereinabove.

In another embodiment of the present invention there is provided a compound according to formula I wherein $R^1$, $R^3$, and $R^4$ are hydrogen; $R^2$ is $COR^5$; and, $R^5$ is as defined hereinabove.

In another embodiment of the present invention there is provided a compound according to formula I wherein $R^1$, $R^3$, and $R^4$ are hydrogen; $R^2$ is $COR^5$; and, $R^5$ is selected from the group consisting of is $C_{1-18}$ unbranched or branched alkyl, $C_{3-8}$ cycloalkyl and optionally substituted phenyl.

In another embodiment of the present invention there is provided a compound according to formula I wherein $R^1$ and $R^2$ are hydrogen; and $R^3$ and $R^4$ are $COR^5$, $C(=O)OR^5$, $C(=O)SR^5$ and $COCH(R^6)NHR^7$; and, in each incidence, $R^5$, $R^6$ and $R^7$ are as defined hereinabove.

In another embodiment of the present invention there is provided a compound according to formula I wherein $R^1$ and $R^2$ are hydrogen; and $R^3$ and $R^4$ are $COR^5$; and, each $R^5$ is independently selected from the group defined hereinabove.

In another embodiment of the present invention there is provided a compound according to formula I wherein $R^1$ and $R^2$ are hydrogen; and $R^3$ and $R^4$ are $COR^5$; and, $R^5$ is independently selected from the group consisting of is $C_{1-18}$ unbranched or branched alkyl, $C_{3-8}$ cycloalkyl and optionally substituted phenyl.

In another embodiment of the present invention there is provided a method of treating a disease mediated by the HCV virus comprising administering a compound according to formula I wherein $R^1$, $R^2$, $R^3$, $R^4$, $R^5$, $R^6$ and $R^7$ are as defined hereinabove In another embodiment of the present invention there is provided a method of treating a disease mediated by the HCV virus comprising administering a compound according to formula I wherein wherein $R^1$ is hydrogen; $R^2$, $R^3$ and $R^4$ are $COR^5$; and each $R^5$ is independently selected from the group consisting of $C_{1-18}$ unbranched or branched lower alkyl, $C_{3-8}$ cycloalkyl, optionally substituted phenyl and $CH_2OPh$.

In another embodiment of the present invention there is provided a method of treating a disease mediated by the HCV virus comprising administering a compound according to formula I wherein wherein $R^1$, $R^3$ and $R^4$ are hydrogen; $R^2$ is $COR^5$; and $R^5$ is selected from the group consisting of $C_{1-18}$ unbranched or branched lower alkyl, $C_{3-8}$ cycloalkyl, optionally substituted phenyl and $CH_2OPh$.

In another embodiment of the present invention there is provided a method of treating a disease mediated by the HCV virus comprising administering a compound according to formula I wherein wherein $R^1$ and $R^4$ are hydrogen; $R^2$ and $R^3$ are $COR^5$; and each $R^5$ is independently selected from the group consisting of $C_{1-18}$ unbranched or branched lower alkyl, $C_{3-8}$ cycloalkyl, phenyl and $CH_2OPh$.

In another embodiment of the present invention there is provided a method of treating a disease mediated by the HCV virus comprising administering a dose of between 1 and 100 mg/kg of body weight of the patient per day of a compound according to formula I wherein wherein $R^1$, $R^2$, $R^3$, $R^4$, $R^5$, $R^6$ and $R^7$ are as defined hereinabove.

In another embodiment of the present invention there is provided a method of treating a disease mediated by the HCV virus comprising co-administering a compound according to formula I wherein wherein $R^1$, $R^2$, $R^3$, $R^4$, $R^5$, $R^6$ and $R^7$ are as defined hereinabove and at least one immune system modulator and/or at least one antiviral agent that inhibits replication of HCV.

In another embodiment of the present invention there is provided a method of treating a disease mediated by the HCV virus comprising co-administering a compound according to formula I wherein wherein $R^1$, $R^2$, $R^3$, $R^4$, $R^5$, $R^6$ and $R^7$ are as defined hereinabove and at least one immune system modulator is interferon, interleukin, tumor necrosis factor or colony stimulating factor.

In another embodiment of the present invention there is provided a method of treating a disease mediated by the HCV virus comprising co-administering a compound according to formula I wherein wherein $R^1$, $R^2$, $R^3$, $R^4$, $R^5$, $R^6$ and $R^7$ are as defined hereinabove and interferon or chemically derivatized interferon.

In another embodiment of the present invention there is provided a method of treating a disease mediated by the HCV virus comprising co-administering a compound according to formula I wherein wherein $R^1$, $R^2$, $R^3$, $R^4$, $R^5$, $R^6$ and $R^7$ are as defined hereinabove and at least one other antiviral agent.

In another embodiment of the present invention there is provided a method of treating a disease mediated by the HCV virus comprising co-administering a compound according to formula I wherein wherein $R^1$, $R^2$, $R^3$, $R^4$, $R^5$, $R^6$ and $R^7$ are as defined hereinabove and at least one other antiviral agent selected from the group consisting of an HCV protease inhibitor, another nucleoside HCV polymerase inhibitor, a non-nucleoside HCV polymerase inhibitor, an HCV helicase inhibitor, an HCV primase inhibitor and an HCV fusion inhibitor.

Several non-nucleoside HCV inhibitors have been described and are currently at various stages of development. The term "non-nucleoside HCV polymerase inhibitor" includes, but is not limited to benzimidazoles (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1); indoles (P. L. Beaulieu et al. WO 03/0010141 A2); benzothiadiazines (D. Dhanak et al. WO 01/85172 A1; D. Dhanak et al. WO 03/037262 A2; K. J. Duffy et al. WO03/099801 A1, J. K. Pratt et al. WO 2004/041818 A1; J. K. Pratt et al. WO 2004/087577 A1), thiophenes (C. K. Chan et al. WO 02/100851 A2); benzothiophenes (D.C. Young and T. R. Bailey WO 00/18231); α-ketopyruvates (S. Attamura et al. U.S. Pat. No. 6,492,423 B1, A. Attamura et al. WO 00/06529); pyrimidines (C. Gardelli et al. WO 02/06246 A1); pyrimidinediones (T. R. Bailey and D. C. Young WO 00/13708); triazines (K.-H. Chung et al. WO 02/079187 A1); rhodanine derivatives (T. R. Bailey and D. C. Young WO 00/10573, J. C. Jean et al. WO 01/77091 A2); 2,4-dioxopyrans (R. A. Love et al. EP 256628 A2); phenylalanine derivatives (M. Wang et al. *J. Biol. Chem.* 2003 278:2489-2495). Combination therapy is intended to maintain pressure on the HCV virus with multiple drugs exhibiting potency against a spectrum strains and mutants which may evolve. Thus combination therapy can be readily envisioned with these or other newly identified anti-HCV compounds and all usch compounds are envisioned with the scope of the present claims.

In another embodiment of the present invention there is provided a pharmaceutical composition for treating a disease mediated by the HCV virus comprising a compound according to formula I wherein wherein $R^1$, $R^2$, $R^3$, $R^4$, $R^5$, $R^6$ and $R^7$ are as defined hereinabove admixed with at least one pharmaceutically acceptable carrier, diluent or excipient.

Definitions

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined hereinabove" refers to the first definition for each group as provided in the Summary of the Invention.

The terms "optional" or "optionally" as used herein means that a described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution.

Compounds of the present invention may have asymmetric centers located on the side chain of a carboxylic ester, amide or carbonate moiety that produce diastereomers when linked to the nucleoside. All stereoisomers of a side chain of compounds of the instant invention are contemplated, either in admixture or in pure or substantially pure form. The definition of the compounds according to the invention embraces all both isolated optical isomers enantiomers and their mixtures including the racemic form. The pure optical isomer can be prepared by sterospecific synthesis from α-D-ribose or the racemic form can be resolved by physical methods, such as, for example, fractional crystallization, separation or crystallization of diastereomeric derivatives or separation by chiral column chromatography. The individual optical isomers can be obtained from the racemates by conventional methods, such as, for example, salt formation with an optically active acid followed by crystallization.

The term "arabinose configuration" as used herein refers configuration corresponding to 2(S), 3(R), 4(R), 5-tetrahydroxypentanal.

The term "alkyl" as used herein denotes an unbranched or branched chain hydrocarbon residue containing 1 to 18 carbon atoms. The term "lower alkyl" denotes an unbranched or branched chain hydrocarbon residue containing 1 to 6 carbon atoms. Representative lower alkyl groups include methyl, ethyl, propyl, i-propyl, n-butyl, i-butyl, t-butyl or pentyl.

When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, trifluoromethyl, trichloromethyl, tribromomethyl, triiodomethyl, 1-fluoroethyl, 1-chloroethyl, 1-bromoethyl, 1-iodoethyl, 2-fluoroethyl, 2-chloroethyl, 2-bromoethyl, 2-iodoethyl, 2,2-dichloroethyl, 3-bromopropyl or 2,2,2-trifluoroethyl.

The term "cycloalkyl" as used herein denotes a saturated carbocyclic ring containing 3 to 8 carbon atoms, i.e. cyclopropyl, cyclobutyl, cyclopentyl, cyclohexyl, cycloheptyl or cyclooctyl.

The term "cycloalkylalkyl" as used herein refers to the radical R'R"—, wherein R' is a cycloalkyl radical as defined herein, and R" is an alkylene radical as defined herein with the understanding that the attachment point of the cycloalkylalkyl moiety will be on the alkylene radical. Examples of cycloalkylalkyl radicals include, but are not limited to, cyclopropylmethyl, cyclohexylmethyl, cyclopentylethyl. $C_{3-7}$ cycloalkyl-$C_{1-3}$ alkyl refers to the radical R'R" where R' is $C_{3-7}$ cycloalkyl and R" is $C_{1-3}$ alkylene as defined herein.

The term "alkylene" as used herein denotes a divalent saturated linear hydrocarbon radical of 1 to 8 carbon atoms or a branched saturated divalent hydrocarbon radical of 3 to 8 carbon atoms, unless otherwise indicated. Examples of alkylene radicals include, but are not limited to, methylene, ethylene, propylene, 2-methyl-propylene, butylene, 2-ethylbutylene.

The term "alkenyl" as used herein denotes an unsubstituted [or substituted] hydrocarbon chain radical having from 2 to 18 carbon atoms, preferably from 2 to 4 carbon atoms, and having one or two olefinic double bonds, preferably one olefinic double bond. Examples are vinyl, 1-propenyl, 2-propenyl (allyl) or 2-butenyl (crotyl).

The term "alkynyl" as used herein denotes an unsubstituted hydrocarbon chain radical having from 2 to 18 carbon atoms, [preferably 2 to 4 carbon atoms], and having one or where possible two triple bonds[, preferably one triple bond]. Examples are ethynyl, 1-propynyl, 2-propynyl, 1-butynyl, 2-butynyl or 3-butynyl.

The term "alkoxy" as used herein denotes an unsubstituted unbranched or branched chain alkyloxy group wherein the "alkyl" portion is as defined above such as methoxy, ethoxy, n-propyloxy, i-propyloxy, n-butyloxy, i-butyloxy, t-butyloxy, pentyloxy, hexyloxy, heptyloxy including their isomers. "Lower alkoxy" as used herein denotes an alkoxy group with a "lower alkyl" group as previously defined.

The term "alkylthio" or "thioalkyl" as used herein denotes a unbranched or branched chain (alkyl)S— group wherein the "alkyl" portion is as defined above. Examples are methylthio, ethylthio, n-propylthio, i-propylthio, n-butylthio, i-butylthio or t-butylthio.

The terms "alkylsulfinyl" and "arylsulfinyl" as used herein denotes a group of formula —S(=O)R wherein R is alkyl or aryl respectively and alkyl and aryl are as defined herein The terms "alkylsulfonyl" and "arylsulfonyl" as used herein denotes a group of formula —S(=O)$_2$R wherein R is alkyl or aryl respectively and alkyl and aryl are as defined herein.

The term "alkoxyalkyl" as used herein denotes an alkoxy group as defined above which is bonded to an alkyl group as defined above. Examples are methoxymethyl, methoxyethyl, methoxypropyl, ethoxymethyl, ethoxyethyl, ethoxypropyl, propyloxypropyl, methoxybutyl, ethoxybutyl, propyloxybutyl, butyloxybutyl, t-butyloxybutyl, methoxypentyl, ethoxypentyl, and propyloxypentyl including their isomers.

The term "hydroxyalkyl" as used herein denotes a unbranched or branched chain alkyl group as defined above wherein 1, 2, 3 or more hydrogen atoms are substituted by a hydroxy group. Examples are hydroxymethyl, 1-hydroxyethyl, 2-hydroxyethyl, 1-hydroxypropyl, 2-hydroxypropyl, 3-hydroxypropyl, hydroxyisopropyl, hydroxybutyl and the like.

The term "aryl" as used herein denotes an optionally substituted monocyclic or polycyclic-aromatic group comprising carbon and hydrogen atoms. Examples of suitable aryl groups include, but are not limited to, phenyl and naphthyl (e.g. 1-naphthyl or 2-naphthyl). Suitable substituents for aryl are selected from the group consisting of alkyl, alkenyl, alkynyl, aryloxy, cycloalkyl, acyl, acylamino, alkoxy, amino, alkylamino, dialkylamino, halogen, haloalkyl, hydroxy, nitro and cyano.

The term "acyl" ("alkylcarbonyl") as used herein denotes a group of formula C(=O)R wherein R is hydrogen, unbranched or branched alkyl containing 1 to 7 carbon atoms or a phenyl group.

The terms "alkoxycarbonyl" and "aryloxycarbonyl" as used herein denotes a group of formula —C(=O)OR wherein R is alkyl or aryl respectively and alkyl and aryl are as defined herein.

The terms "thioalkylcarbonyl" and "arylthiocarbonyl" as used herein denotes a group of formula —C(=O)SR wherein R is alkyl or aryl respectively and alkyl and aryl are as defined herein The term halogen stands for fluorine, chlorine, bromine or iodine, preferably fluorine, chlorine, bromine.

The term "amino acid" as used herein refers to naturally occurring α amino carboxylic acids, as well as to optical isomers (enantiomers and diastereomers), synthetic analogs and derivatives thereof. α-Amino acids comprise a carbon atom bonded to a carboxyl group, an amino group, a hydrogen atom and a unique "side chain" group. The term "naturally occurring amino acids" means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, γ-carboxyglutamic acid, arginine, ornithine and lysine. The side chains of naturally occurring amino acids include: hydrogen, methyl, iso-propyl, iso-butyl, sec -butyl, —CH$_2$OH, —CH(OH)CH$_3$, —CH$_2$SH, —CH$_2$CH$_2$SMe, —(CH$_2$)$_p$COR wherein R is —OH or —NH$_2$ and p is 1 or 2, —(CH$_2$)$_q$—NH$_2$ where q is 3 or 4, —(CH$_2$)$_3$—NHC(=NH)NH$_2$, —CH$_2$C$_6$H$_5$, —CH$_2$-p-C$_6$H$_4$—OH, (3-indolinyl)methylene, (4-imidazolyl)methylene.

The term "acylating agent" as used herein refers to either an anhydride, acyl halide or other activated derivative of a carboxylic acid. The term "anhydride" as used herein refers to compounds of the general structure RC(O)—O—C(O)R wherein is as defined in the previous paragraph. The term "acyl halide" as used herein refers to the group RC(O)X wherein X is bromo or chloro. The term "activated derivative" of a compound as used herein refers to a transient reactive form of the original compound which renders the compound active in a desired chemical reaction, in which the original compound is only moderately reactive or non-reactive. Activation is achieved by formation of a derivative or a chemical grouping within the molecule with a higher free energy content than that of the original compound, which renders the activated form more susceptible to react with another reagent. In the context of the present invention activation of the carboxy group is of particular importance. The term acylating agent as used herein further includes reagents that produce carbonates (—OC(=O)OR$^5$, carbamates (—NHC(=O)OR$^5$), thiocarbonate(—OC(=O)SR$^5$), and thiocarbamate (—NHC(=O)SR$^5$), derivatives such as alkoxychlorocarbonates, R$^5$OC(=O)Cl, and alkylthiochlorocarbonates, R$^5$SC(=O)Cl, wherein R$^5$ is as defined hereinabove.

The term "protecting group" as used herein means a chemical group that (a) preserves a reactive group from participating in an undesirable chemical reaction; and (b) can be easily removed after protection of the reactive group is no longer required. For example, the trialkylsilyl is a protecting group for a primary hydroxyl function and an acetonide is a protecting group for a vicinal diol.

In the pictorial representation of the compounds given throughout this application, a thickened tapered bond (◤) indicates a substituent which is above the plane of the ring to which the asymmetric carbon belongs (also designated β) and a dotted bond (⋯⋯) indicates a substituent which is below the plane of the ring to which the asymmetric carbon belongs (also designated α).

The term "combination" or "combination therapy" as used herein in reference in administering a plurality of drugs in a therapeutic regimen by concurrent or sequential administration of the drugs at the same time or at different times.

The term "chemically-derivatized interferon" as used herein refers to an interferon molecule covalently linked to a polymer which alters the physical and/or pharmacokinetic properties of the interferon. A non-limiting list of such polymers include polyalkylene oxide homopolymers such as polyethylene glycol (PEG) or polypropylene glycol (PPG), polyoxyethylenated polyols, copolymers thereof and block copolymers thereof, provided that the water solubility of the block copolymers is maintained. One skilled in the art will be aware of numerous approaches to linking the polymer and interferon (for example, see A. Kozlowski and J. M. Harris *J. Control. Release* 2001 72(1-3):217-24). A non-limiting list of chemically derivatized IFNα contemplated in the present patent include peginterferon-α-2a (PEGASYS®) and peginterferon-α-2b (PEGINTRON®).

Compounds of formula I exhibit tautomerism. Tautomeric compounds can exist as two or more interconvertible species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(=O)—CH— ⇌ —C(—OH)=CH—), amide/imidic acid (—C(=O)—NH— ⇌ —C(—OH)=N—) and amidine (—C(=NR)—NH— ⇌ —C(—NHR)=N—) tautomers. The latter two are particularly common in heteroaryl and heterocyclic rings and the present invention encompasses all tautomeric forms of the compounds.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

The term "hydrate" as used herein means a compound of the invention or a salt thereof, that further includes a stoichiometric or non-stoichiometric amount of water bound by non-covalent intermolecular forces.

The term "clathrate" as used herein means a compound of the invention or a salt thereof in the form of a crystal lattice that contains spaces (e.g., channels) that have a guest molecule (e.g., a solvent or water) trapped within.

Abbreviations used in this application include: acetyl (Ac), acetic acid (HOAc), azo-bis-isobutyrylnitrile (AIBN), 1-N-hydroxybenzotriazole (HOBT), atmospheres (Atm), high pressure liquid chromatography (HPLC), 9-borabicyclo[3.3.1]nonane (9-BBN or BBN), methyl (Me), tert-butoxycarbonyl (Boc), acetonitrile (MeCN), di-tert-butyl pyrocarbonate or boc anhydride ($BOC_2O$), 1-(3-dimethylaminopropyl)-3-ethylcarbodiimide hydrochloride (EDCI), benzyl (Bn), m-chloroperbenzoic acid (MCPBA), butyl (Bu), methanol (MeOH), benzyloxycarbonyl (cbz or Z), melting point (mp), carbonyl diimidazole (CDI), $MeSO_2$— (mesyl or Ms), 1,4-diazabicyclo[2.2.2]octane (DABCO), mass spectrum (ms) diethylaminosulfur trifluoride (DAST), methyl t-butyl ether (MTBE), dibenzylideneacetone (Dba), N-carboxyanhydride (NCA), 1,5-diazabicyclo[4.3.0]non-5-ene (DBN), N-bromosuccinimide (NBS), 1,8-iazabicyclo[5.4.0]undec-7-ene (DBU), N-methylpyrrolidone (NMP), 1,2-dichloroethane (DCE), pyridinium chlorochromate (PCC), N,N'-dicyclohexylcarbodiimide (DCC), pyridinium dichromate (PDC), dichloromethane (DCM), propyl (Pr), diethyl azodicarboxylate (DEAD), phenyl (Ph), di-iso-propylazodicarboxylate, DIAD, pounds per square inch (psi), diethyl iso-propylamine (DEIPA), pyridine (pyr), di-iso-butylaluminiumhydride, DIBAL-H, room temperature, rt or RT, N,N-dimethyl acetamide (DMA), tert-butyldimethylsilyl or t-$BuMe_2Si$, (TBDMS), 4-N,N-dimethylaminopyridine (DMAP), triethylamine ($Et_3N$ or TEA), N,N-dimethylformamide (DMF), triflate or $CF_3SO_2$— (Tf), dimethyl sulfoxide (DMSO), trifluoroacetic acid (TFA), 1,1'-bis-(diphenylphosphino)ethane (dppe), 2,2,6,6-tetramethylheptane-2,6-dione (TMHD), 1,1'-bis-(diphenylphosphino)ferrocene (dppf), thin layer chromatography (TLC), ethyl acetate (EtOAc), tetrahydrofuran (THF), diethyl ether ($Et_2O$), trimethylsilyl or $Me_3Si$ (TMS), ethyl (Et), p-toluenesulfonic acid monohydrate (TsOH or pTsOH), lithium hexamethyl disilazane (LiHMDS), 4-Me-$C_6H_4SO_2$— or tosyl (Ts), iso-propyl (i-Pr), N-urethane-N-carboxyanhydride (UNCA), ethanol (EtOH). Conventional nomenclature including the prefixes normal (n), iso (i-), secondary (sec-), tertiary (tert-) and neo have their customary meaning when used with an alkyl moiety. (J. Rigaudy and D. P. Klesney, *Nomenclature in Organic Chemistry*, IUPAC 1979 Pergamon Press, Oxford.).

Compounds and Preparation

Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, Volumes 1-21; R. C. LaRock, *Comprehensive Organic Transformations*, $2^{nd}$ edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

SCHEME 1

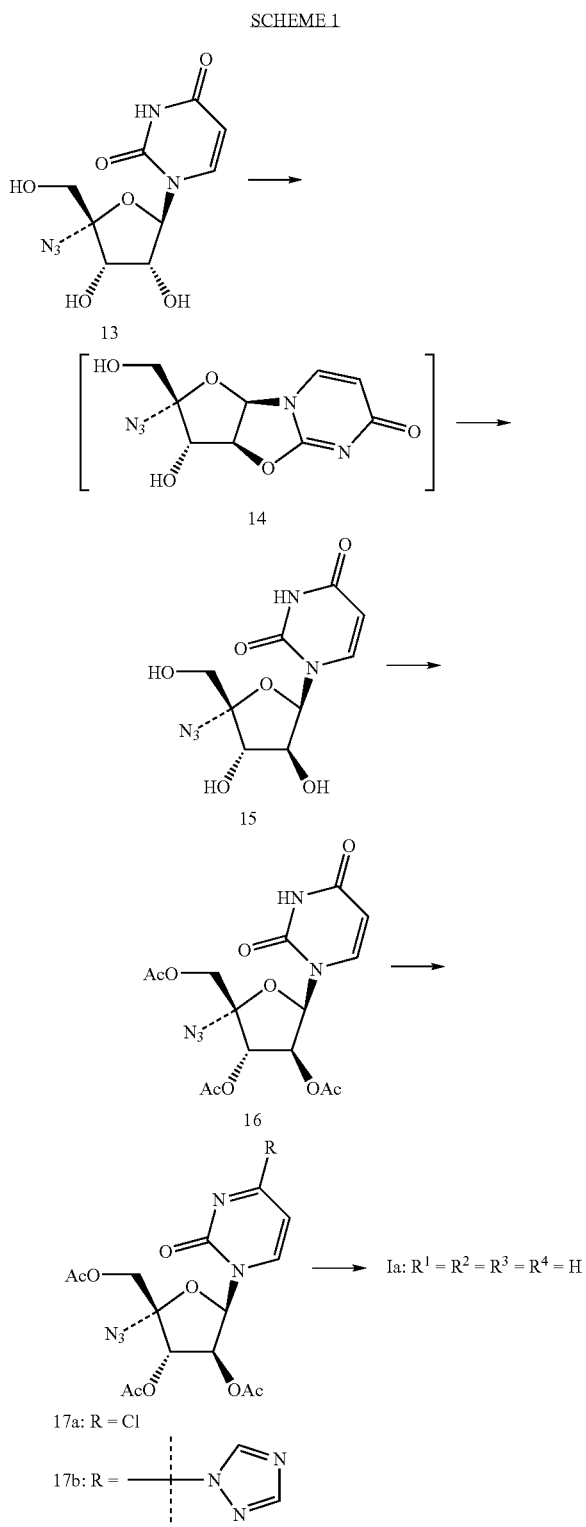

Compounds of the present invention can be prepared from 4-amino-1-((2R,3R,4S,5R)-5-azido-3,4-dihydroxy-5-hydroxymethyl-tetrahydro-furan-2-yl)-1H-pyrimidin-2-one (13; R. R. Devos et al. WO02/100415) by inversion of the 2'-α-hydroxy via the 2,2'-anhydro sugar 14. (T. Ueda in *Chemistry of Nucleosides and Nucleotides*, L. B. Townsend (ed) v 1, Plenum Press, New York 1988 pp 50-53; A. Hampton and A. W. Nichol *Biochemistry* 1966 5(6):2076-2082). Anhydro nucleosides undergo hydrolysis under mild acidic or basic conditions (J. P. H. Verheyden et al. *J. Org. Chem.* 1971 36(2):250-254) which affords 4'azido-ara-U (Ara-U as used herein refers to 1-β-D-arabinofuranosyl-uracil. Ara-C refers to D-arabinofuranosyl-cytosine) 15.

Conversion of the ara-U (15) to the corresponding ara-C (I: $R^1$-$R^4$=H) can be carried out by standard procedures. The conversion of uridines to cytidines by addition of triazoles 17b has been described by Maag et al. (supra), A. D. Borthwick et al. (*J. Med. Chem.* 1990, 33(1):179) and Divakar and Reese (*J. Chem Soc., Perkin Trans.* 1 11982 1171-1176). After protection of the hydroxyl groups on the nucleoside, the 4-carbonyl of the base is converted to a leaving group which is displaced with ammonia. SCHEME 1 depicts an exemplary sequence wherein treatment with a mixture of 1,2,4-triazole, $POCl_3$ and TEA affords 17b. Displacement of the triazole with ammonia and cleavage of the triesters were accomplished by reacting 17b with ammonium hydroxide to afford 4'-azido-ara-cytidine (I-1).

While nucleosides frequently exhibit high levels of biological activity; however, their practical utility is often limited by suboptimal physical properties and poor pharmacokinetics. The embodiments of the present invention further relate to prodrugs of 4'-azido-ara-C nucleosides with improved physiochemical and pharmacokinetic properties. These derivatives more efficiently permeate the intestinal mucosa whereupon a variety of enzymes present in the cytoplasm, blood, or serum convert the derivative to the parent nucleoside. These "prodrugs" or "pronucleotides" can improve the properties such as activity, bioavailability or stability of the parent nucleotide.

The term "prodrug" or "pro-nucleotide" as used herein means a pharmacologically inactive form of a compound which must be metabolized in vivo, e.g., by biological fluids or enzymes, by a subject after administration into a pharmacologically active form of the compound in order to produce the desired pharmacological effect. Prodrugs of a compound of Formula I are prepared by modifying one or more hydroxyl group(s) and/or amino groups present in the compound of Formula I in such a way that the modification(s) may be cleaved in vivo to release the parent compound. Prodrugs include compounds of Formula I wherein one or more hydroxy groups in the compound of Formula I is bonded to any group that may be cleaved in vivo to regenerate the free hydroxyl group(s). Examples of prodrugs include, but are not limited to, esters (e.g. acetate, dialkylaminoacetates, formates, phosphates, sulfates and benzoate derivatives) and carbamates of hydroxy functional groups (e.g. N,N-dimethylcarbonyl), esters of carboxyl functional groups (e.g. ethyl esters, morpholinoethanol esters), N-acyl derivatives (e.g. N-acetyl), N-Mannich bases, Schiff bases and enaminones of amino functional groups, oximes, acetals, ketals, and enol esters of ketones and aldehyde functional groups in compounds of Formula I and the like.

The prodrug can be metabolized before absorption, during absorption, after absorption, or at a specific site. Although metabolism occurs for many compounds primarily in the liver, almost all other tissues and organs, especially the lung, are able to carry out varying degrees of metabolism. Prodrug forms of compounds may be utilized, for example, to improve bioavailability, improve subject acceptability such as by masking or reducing unpleasant characteristics such as bitter taste or gastrointestinal irritability, alter solubility such as for intravenous use, provide for prolonged or sustained release or delivery, improve ease of formulation, or provide site-specific delivery of the compound. Reference to a compound herein includes prodrug forms of a compound. Prodrugs are described in *The Organic Chemistry of Drug Design and Drug Action*, by Richard B. Silverman, Academic Press, San Diego, 1992; Chapter 8: "Prodrugs and Drug delivery Systems" pp. 352-401; *Design of Biopharmaceutical Properties through Prodrugs and Analogs*, Ed. by E. B. Roche, American Pharmaceutical Association, Washington, 1977; *Drug Delivery Systems*, ed. by R. L. Juliano, Oxford Univ. Press, Oxford, 1980; Ettmayer et al., *J. Med. Chem.* 2004 47(10):2393-2404; K. Beaumont et al., *Curr. Drug Metab.* 2003 4:461-485; H. Bundgaard, *Design of Prodrugs: Bioreversible derivatives for various functional groups and chemical entities in Design of Prodrugs*, H. Bundgaard (ed) Elsevier Science Publishers, Amsterdam 1985; and G. M. Pauletti et al. *Adv. Drug Deliv. Rev.* 1997 27:235-256; K. Beaumont et al. *Curr. Drug Metab.* 2003 4:461-485).

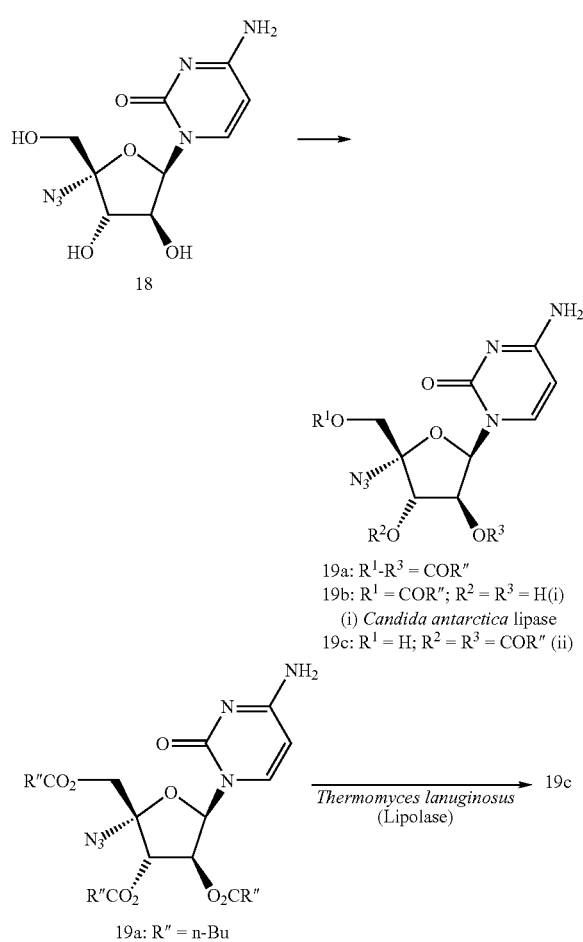

Triacyl derivatives of 4'-azido-ara-C 19a can be prepared by acylation of 18. The acylation is conveniently carried out with a corresponding acyl halide or anhydride in a solvent such as DCM, chloroform, carbon tetrachloride, ether, THF, dioxane, benzene, toluene, MeCN, DMF, sodium hydroxide solution or sulpholane optionally in the presence of an inorganic or organic base at temperatures between −20 and 200° C., but preferably at temperatures between −10 and 160° C.

The acylation may, however, also be carried out with the free acid optionally in the presence of an acid -activating agent or a dehydrating agent, e.g. in the presence of isobutyl chloroformate, $SOCl_2$, trimethylchlorosilane, HCl, $H_2SO_4$, methanesulphonic acid, p-toluenesulphonic acid, $PCl_3$, $P_2O_5$, DCC, DCC/N-hydroxysuccinimide or HOBt, N,N'-carbonyldiimidazole, O-(benzotriazol-1-yl)-N,N,N',N'-tetramethyluronium $BF_4^-$/NMM, O-(benzotriazol-1-yl)-N,N,N',N'-tetramethyl-uronium $BF_4^-$/DIPEA, N,N'-thionyldimidazole or $Ph_3P/CCl_4$, at temperatures between −20 and 200° C., but preferably at temperatures between −10 and 160° C. The acylation reaction also may be carried out under Schotten Baumann in biphasic aqueous medium.

The triisobutyroyl derivative 19a (R"=i-Pr) was prepared as described in Example 3 using isobutyric anhydride. Other triacyl derivatives can be prepared in analogous manner using an appropriate acid chloride or anhydride. One skilled in the art can, with minimal experimentation, adapt the conditions to suit the physical properties and reactivity which may be exhibited of other acylating agents Amino acid esters can be prepared utilizing numerous protocols refined for peptide synthesis. Prior to carrying out the esterification step with an amino acid, the amino group of the amino acid must be protected to prevent undesirable amide formation. Various N-protecting groups have been developed which can be selectively cleaved under a variety of conditions. Protection strategies for coupling amino acids have been extensively reviewed (see e.g., M. Bodanszky, *Principles of Peptide Synthesis*, Springer Verlag, New York 1993; P. Lloyd-Williams and F. Albericio *Chemical Methods for the Synthesis of Peptides and Proteins* CRC Press, Boca Raton, Fla. 1997). These references are incorporated herein in their entirety. The various amino-protecting groups useful in this invention include N-benzyloxy-carbonyl-(cbz), tert-butoxy-carbonyl (Boc), N-formyl- and N-urethane-N-carboxy anhydrides which are all commercially available (SNPE Inc., Princeton, N.J., Aldrich Chemical Co., Milwaukee, Wis., and Sigma Chemical Co., St. Louis, Mo.) N-urethane amino-protected cyclic amino acid anhydrides are also described in the literature (William D. Fuller et al., *J. Am. Chem. Soc.* 1990 112:7414-7416) which is incorporated herein by reference. While many of these could be effectively employed in the present process, preferred urethane protecting groups include the tert-butoxycarbonyl or the benzyloxycarbonyl.

Various reagents have been described to activate the amino acid prior to carrying out the esterification step. Protocols for efficient coupling of N-protected amino acids have been refined and extensively optimized (M. Bodanszky supra; P. Lloyd-Williams and F. Albericio supra). At least 1 equivalent of the protected amino acid and 1 equivalent of a suitable coupling agent or dehydrating agent, e.g., 1,3-dicyclohexylcarbodiimide or salts of such diimides with basic groups, N-ethyl-N'-(3-(dimethylamino)propyl)carbodiimide hydrochloride, should be employed from the start. Other dehydrating agents such as DCC, trifluoroacetic anhydride, mixed anhydrides, acid chlorides may be used. Numerous additives have been identified which improve the coupling efficiency and limit racemization of the alpha-amino acid including, hobW and 3-hydroxy-3,4-dihydro-4-oxo-1,2,3-benzotriazine (W. König and R. Geiger *Chem. Ber.* 1970 788:2024 and 2034), N-hydroxysuccinimide (E. Wunsch and F. Drees, *Chem. Ber.* 1966 99:110), 1-hydroxy-7-azabenzotriazole (L. A. Carpino *J. Am. Chem. Soc.* 1993 115:4397-4398). Aminium/uronium- and phosphonium HOBt/HOAt-based coupling reagents have been developed, e.g based peptide coupling reagents, e.g., 1-benzotriazol-1- yloxy-bis(pyrrolidino)uronium hexafluorophosphate (J. Xu and S. Chen *Tetrahedron Lett.* 1992 33:647), 1-benzotriazol-1-yloxy-N,N-dimethylmethananiminium hexachloroantimonate (P. Li and J. Xu, *Tetrahedron Lett.* 1999 40:3606), O-(7-azabenzotriazol-1-yl)-1,1,3,3-tetramethylammoniumuronium hexafluorophosphate (L. A. Carpino, *J. Am. Chem. Soc.* 1993 115:4397), O-(7-azabenzotriazol-1-yl)-1,1,3,3-bis-(tetramethylene)uronium hexafluorophosphate (A. Erlich et al. *Tetrahedron Lett.* 1993 34:4781), 2-(3,4-dihydro-4-oxo-1,2,3-benzotriazin-3-yl)-1,1,3,3-tetramethyluronium tetrafluoroborate (R. Knorr et al. *Tetrahedron Lett.* 1989 30:1927), 7-azobenzotriazolyoxy-tris-(pyrrolidino)hexafluorophosphate (F. Albericio et al., *Tetrahedron Lett.* 1997 38:4853), 1-benzotriazolyloxy-tris-(dimethylamino)phosphonium hexafluorophosphate (B. Castro et al. *Tetrahedron Lett.* 1976 14:1219) and, 1-benzotriazoloxy-trispyrrolidinophosphonium hexafluorophosphate (J. Coste et al. *Tetrahedron Lett.* 1990 31:205).

Particularly useful for the present invention are N-urethane-N-carboxy anhydrides (UNCA's) (William D. Fuller et al. *J. Am. Chem. Soc.* 1990 112:7414-7416, which is incorporated herein by reference). Other protected amino acid N-carboxy anhydrides are described in PCT Patent Application WO 94/29311. UNCA's (22) do not require an activation step prior to coupling. The formation of $CO_2$ during the coupling irreversibly drives the coupling reaction. Alternative coupling reagents can be readily identified without undo experimentation. The 5'-valine monoester was prepared by selective acylation of 18 with the N-carboxyanhydride of BOC-valine under Schotten-Baumann conditions.

Selective acylation of the specific hydroxyl groups on the carbohydrate radical can be conveniently accomplished by enzyme catalyzed acylations or deacylations. Enzyme catalysis provides mild selective conditions for organic transformations. S. M. Roberts has reviewed preparative biotransformations (*J. Chem. Soc. Perkin* 1, 2001, 1475; 2000 611; 1999, 1; and, 1998 157). M. Mahmoudian et al. (*Biotechnol. Appl. Biochem.* 1999 29:229-233) reported the selective acylation of the 5'-position of 2-amino-9-β-D-arabinfuranosyl-6-methoxy-9H-purine with Novozyme 435, an immobilized preparation of *Candida antarctica* lipase. Other enzymes reported to selectively acylate the 5'-hydroxyl include: *Bacillus licheniformis* protease, Lipozyme IM (*Mucor miehei* lipase, CLEC-BL (*B. licheniformis* protease), savinase (*Bacillus* sp. protease), Novozyme-243 (*Bacillus licheniformis* protease), *Alcaligenes* sp. lipase and lipolase (Novo).

Lipolase® enzyme preparation (lipase from *Thermomyces lanuginosus*, Sigma catalog # L 0777) was found to selectively hydrolyze the 5'-acyl group of triacyl derivatives to afford 2',3'-diacyl compounds. In WO2004043894, G. G. Heraldsson et al. disclose the use of *T. lanuginosus* lipase for esterification of marine oils. N. Weber et al. (*Eur. J. of Lipid Sci. and Technol.* 2003 105(10):624-626) disclose *T. lanuginosus* catalyzed transesterification of methyl oleate. V. Bodai et al. (*Adv. Synth. Cat.* 2003 345(6 and 7):811-818) describe novel hydrolases from thermophilic filamentous fungi which can be used for selective biotransformations.

Other reports of regioselective enzymatic ester hydrolysis include: R. Hanson et al., *Bioorg. and Med. Chem.* 2000, 2681-2687 (synthesis of a lobucavir prodrug via regioselective acylation and hydrolysis); R. Pfau et al., *Syn Lett* 1999, 1817-1819 (selective hydrolysis of carbohydrate ester); A. Bianco et al, *J. of Mol. Cat. B: Enzymatic* 1997 209-212 (regioselective acylation and hydrolysis for synthesis of sialic acid derivatives); Y. Ota et. al., Bioscience, Biotechnology, Biochemistry (1997), 166-167 (regioselective ester hydrolysis of 1,2,3-trihexanolylglycerol); U. T. Bomscheuer et al., Enzyme Microbial Technol. 1995, 578-86 (lipase catalyzed syntheses of monoacylglycerol; review); C. T. Goodhue et al. WO9403625 (regioselective process for resolution of carbohydrate monoesters); N. W. Boaz, WO9115470 (Separation of alcohol-ester mixture by selective enzymatic hydrolysis); Y. S. Sanghvi et al. U.S. 2002142307 (regioselective hydrolysis of 3',5'-di-O-levulinylnucleosides); J. Garcia et al. *J. Org. Chem.* 2002, 4513-4519 (regioselective hydrolysis of 3',5'-di-O-levulinylnucleosides); O. Kirk et al. *Biocat and Biotransformation* (1995) 91-7 (lipase catalyzed regioselective acylation and deacylation of glucose derivatives) etc.

One skilled in the art will recognize that the selective esterifications can also be accomplished by standard chemical methodology. Selective protection of the 5'-hydroxyl group has been described which will allow direct esterification of the 2'- and 3'-hydroxyls or alternative incorporation of a second protecting group which will allow deprotection and selective acylation of the primary alcohol.

TABLE 1

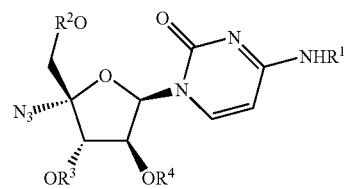

(I)

| | $R^1$ | $R^2$ | $R^3$ | $R^4$ | Mw | ms [M + H]⁺ | mp (° C.) |
|---|---|---|---|---|---|---|---|
| I-1 | H | H | H | H | 284.23 | 285 | |
| I-2[1] | H | CO-i-$C_3H_7$ | CO-i-$C_3H_7$ | CO-i-$C_3H_7$ | 494.50 | | 167-169 |
| I-3 | H | CO-n-$C_4H_9$ | CO-n-$C_4H_9$ | CO-n-$C_4H_9$ | 536.58 | | 145-146 |
| I-4 | H | CO-n-$C_3H_7$ | CO-n-$C_3H_7$ | CO-n-$C_3H_7$ | 494.50 | | 131-137 |
| I-5 | H | H | CO-n-$C_4H_9$ | CO-n-$C_4H_9$ | 452.46 | | 160.4-162.2 |
| I-6 | H | CO-n-$C_{11}H_{23}$ | H | H | 456.54 | 467 | 108.3-125.6 |
| I-7 | H | N-Boc-L-Val | H | H | 483.48 | 484 | 106.9-107.3 |
| I-8 | H | CO-n-$C_{13}H_{27}$ | H | H | 494.59 | | 110.3-119.3 |
| I-9 | H | CO-n-$C_{15}H_{31}$ | H | H | 522.64 | 523 | 110.5-113 |

TABLE 1-continued (I)

[Structure: pyrimidine nucleoside analog with R²O-CH2, N3, OR³, OR⁴ on sugar; N-NHR¹ on cytosine-like base]

| | R¹ | R² | R³ | R⁴ | Mw | ms [M + H]⁺ | mp (° C.) |
|---|---|---|---|---|---|---|---|
| I-10 | H | CO-n-C₉H₁₉ | H | H | 438.48 | 439 | 100.5-102.1 |
| I-11 | CO₂-n-C₇H₁₅ | H | H | H | 426.43 | 428 | 162.6-164.8 |
| I-12 | CO₂-n-C₈H₁₇ | H | H | H | 440.45 | 441 | 148.2-149.9 |
| I-13 | CO₂-n-C₁₀H₂₁ | H | H | H | 468.51 | 469 | 127.0-130.7 |

¹Compound isolated as the mesylate salt.

Dosage and Administration

The compounds of the present invention may be formulated in a wide variety of oral administration dosage forms and carriers. Oral administration can be in the form of tablets, coated tablets, dragées, hard and soft gelatine capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use.

The term "excipient" as used herein includes both one and more than one such excipient.

A pharmaceutically acceptable salt form of an active ingredient may also initially confer a desirable pharmacokinetic property on said active ingredient which it did not previously possess, and may even positively affect the pharmacodynamics of said active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. Compounds of formula I which are basic can form pharmaceutically acceptable salts with acids. The formation and isolation of such salts can be carried out according to methods known in the art.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 100 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In general a therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necro-inflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

It has been recognized that drug-resistant variants of HCV can emerge after prolonged treatment with an antiviral agent. Drug resistance most typically occurs by mutation of a gene that encodes for an enzyme used in viral replication, and most typically in the case of HIV, reverse transcriptase, protease, or DNA polymerase, and in the case of HCV, DNA polymerase. Other anti-viral therapy demonstrated that the efficacy of a drug can be prolonged, augmented, or restored by administering the compound in combination or alternation with a second, and perhaps third, antiviral compound that induces a different mutation from that caused by the principle drug. Alternatively, the pharmacokinetics, biodistribution, or other parameter of the drug can be altered by such combination or alternation therapy. In general, combination therapy is typically preferred over alternation therapy because it induces multiple simultaneous stresses on the virus.

The second antiviral agent for the treatment of HCV, in one embodiment, can be a HCV polymerase inhibitor, which can be either a synthetic nucleoside or a non-nucleoside compound. In an alternative embodiment, in the case of HCV, the second (or third) antiviral agent can be a protease inhibitor.

When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

EXAMPLE 1

1-((2R,3R,4S,5R)-5-Azido-3,4-dihydroxy-5-hydroxymethyl-tetrahydro-furan-2-yl)-1H-pyrimidine-2,4-dione (13)

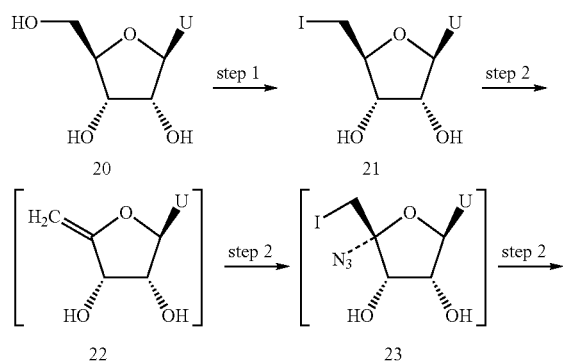

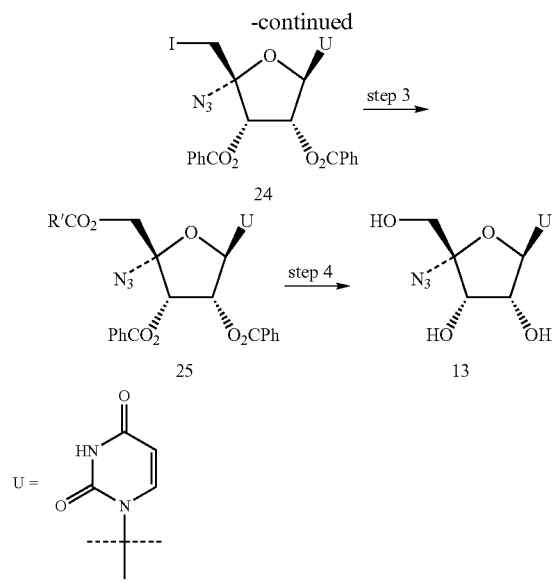

step 1-1-((2R,3R,4S,5S)-3,4-Dihydroxy-5-iodomethyl-tetrahydro-furan-2-yl)-1H-pyrimidine-2,4-dione Uridine (20; 30.0 kg), TPP (46.8 kg) and imidazole (12.2 kg) were slurried in THF (267 kg). A solution of iodine (33.2 kg) in THF (87 kg) was added slowly to the slurry while the reaction temperature was maintained below 28° C. The reaction mixture was stirred overnight (ca. 18 h) at about 25° C. to achieve complete conversion. The reaction mixture was quenched with a small amount (2.3 L) of water. The reaction mixture was distilled under moderate vacuum while adding isopropanol (maximum internal temperature: 50° C.) till IPA content (by gc) of the distillate was greater than 87% (v/v). The resulting slurry was cooled to room temperature (ca. 22° C.) and aged overnight. The precipitated product was filtered and washed with isopropanol (2×50 kg) and dried at about 50° C. under vacuum with a slow nitrogen stream to afford 21 (36.5 kg; 83.9% theory.).

step 2-Benzoic acid (2S,3S,4R,5R)₄-benzoyloxy-2-azido-5-(2,4-dioxo-3,4-dihydro-2H-pyrimidin-1-yl)-2-iodomethyl-tetrahydro-furan-3-yl ester A suspension of 21 (12.0 kg) in MeOH (68 kg) was treated with 25% sodium methoxide solution (18.4 kg) to obtain a clear solution, which was allowed to stand at about 60° C. for about 2 h to achieve complete conversion. The reaction mixture was then added to a solution of N-methylmorpholinium mesylate in methanol (prepared in situ by adding 8.9 kg of NMM to a solution of 8.1 kg of methanesulfonic acid in 19 kg of MeOH). The reaction mixture was concentrated in vacuo (internal temp <40° C.) and the evaporated MeOH was replaced with THF (batch volume ca. 50 L) to until the residual methanol level was ca. 1-2% (by gc). The resulting slurry of crude 22 was diluted with acetonitrile (20 kg) and made slightly basic with NMM (1.2 kg). Benzyl triethylammonium chloride (10.0 kg) and sodium azide (2.87 kg) were slurried together in acetonitrile (45 kg) to extract azide into acetonitrile as the quaternary ammonium azide. The slurry was filtered, and the quaternary azide solution was added to the slurry of crude 22. A solution of iodine (11.2 kg) in THF (40 kg) was then added slowly to the resulting slurry while maintaining batch temperature at 0-5° C. After completion of addition, the reaction mixture was allowed to stand at 5-10° C. for 18-24 hours to complete the conversion to 23.

To the reaction mixture was added TEA (17.2 kg) and DMAP (0.41 kg), and the mixture cooled to about −10° C. and treated with benzoyl chloride (14.3 kg) while maintaining the internal temperature below −5° C. After the addition was completed, the reaction mixture was allowed to stand at ca. −5° C. until benzoylation was complete. The reaction mixture was quenched with water and aqueous sodium sulfite (to destroy residual iodine) solution and treated with EtOAc (44 kg) was added. The organic phase was washed with water and water back-extracted with EtOAc (44 kg) and the combined organic extracts concentrated under reduced pressure (maximum jacket temperature: 65° C.) and the evaporated solvents were replaced with isopropanol from which 24 crystallized. The resulting slurry is cooled to ca. 20° C. and allowed to stand for at least 2 h. The precipitated product was isolated by filtration, washed with isopropanol and dried at 25-50° C. under a vacuum in a stream of nitrogen to yield 24 (15.9 kg; overall yield 77.6% theoretical)

step 3-3-Chloro-benzoic acid (2R,3S,4R,5R)-2-azido-3,4-bis-benzoyloxy-5-(2,4-dioxo-3,4-dihydro-2H-pyrimidin-1-yl)-tetrahydro-furan-2-ylmethyl ester A mixture of 24 (14.2 kg), tetrabutyl ammonium hydrogen sulfate (8.5 kg), potassium hydrogen phosphate (8.5 kg), m-chlorobenzoic acid (4.0 kg), DCM (70 kg) and water (28 kg) was charged to a slurry of m -chloroperbenzoic acid (22.4 kg) in DCM (70 kg). The mixture was stirred at room temperature until the reaction was complete (by HPLC). To quench the reaction, the reaction mixture a solution of sodium sulfite (19 kg) in water (70 kg) was added while maintaining temperature below 25° C. After a stirring for a short time, a solution of potassium carbonate (28 kg) in water (51 kg) was added. The lower organic layer is separated and concentrated under atmospheric pressure. The DCM was replaced with isopropanol. The resulting solution (vol. 40-50 L) was treated with hot water (70 L) which resulted in the precipitation of the desired product. The resulting slurry was warmed to about 65° C. for 2 h and then allowed to cool to room temperature. The precipitated product was isolated by filtration, washed with a mixture of isopropanol and water and dried under vacuum at about 50° C. to afford 25 (10.6 kg; 71.3% theory)

step 4-4'-azido-uridine (13)

A suspension of 25 (2.0 kg) in methanol (8.5 L) is treated with methanolic ammonia (7 N, 2.5 L) and stirred for ca. 16 h at ambient temperature. The reaction mixture is concentrated under reduced pressure and then treated with acetone (2.5 L) and hexane(s) (1.5 L) to precipitate the product. The resulting slurry is heated up to 50° C. and more hexane(s) (5 L) is added slowly. The resulting mixture is aged at 50° C. for 2 hours and cooled to ambient temperature and stirred overnight. The precipitated product is filtered out and washed with acetone/hexane (1:4, v/v, 3×0.7 L), and dried at 60° C. in vacuo to afford 13 (887 g, 98.6% theory) as an off-white solid: m.p. 110-115° C.; $^1$H-NMR (D$_2$O, 300 MHz): δ 7.67 (d, 1H, $J_{5,6}$=8.1 Hz, H6); 5.97 (d, 1H, $J_{1',2'}$=3.8 Hz, H1'); 5.80 (d, 1H, H5); 4.69 (s, 4H, 3×OH and NH); 4.43 (dd, 1H, $J_{2',3'}$=6.2 Hz, H2'); 4.33 (d, 1H, H3'); ); 3.77 (q, 2H, $J_{5'a,5'b}$=12.6 Hz, H$_5$'a, H5'b); $^{13}$C-NMR: δ166.4, 151.6, 142.8, 102.8, 99.0, 92.2, 72.7, 71.1 and 63.4.

Example 2

4-Amino-1-((2R,3S,4S,5R)-5-azido-3,4-dihydroxy-5-hydroxymethyl-tetrahydro-furan-2yl)-1H-pyrimidin-2-one (I-1)

step 1

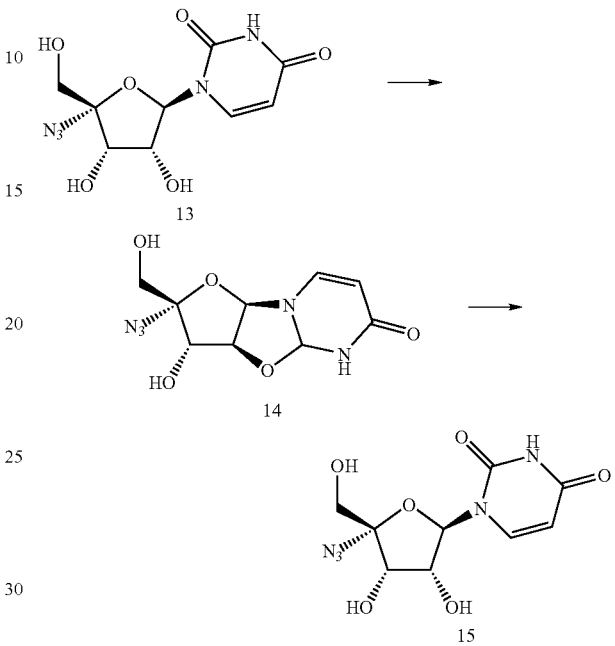

A mixture of 4'-azidouridine (13, 1.00 g, 3.50 mmol), diphenylcarbonate (0.826 g, 3.85 mmol), HaHCO$_3$ (0.015 g) and DMF (1 mL) was heated to 110° C. (oil bath temperature) under an atmosphere of nitrogen. After 14 h the reaction mixture was cooled to RT and diluted with MeCN (5 mL). The resulting precipitate 14 was removed by filtration (0.85 g, off-white solid product corresponds to 2'-anhydrouridine by $^1$ H NMR).

Crude 2'-anhydrouridine 14 was treated with EtOH (10 mL) and 1 M NaOH solution (2 mL) and stirred at room temperature for 3 h. The reaction solution was acidified with Amberlyst 15 ion exchange resin, filtered and then evaporated to dryness under reduced pressure to give 4'-azidoarabinouridine (15, 0.83 g, 83%) as an off-white foam.

step 2

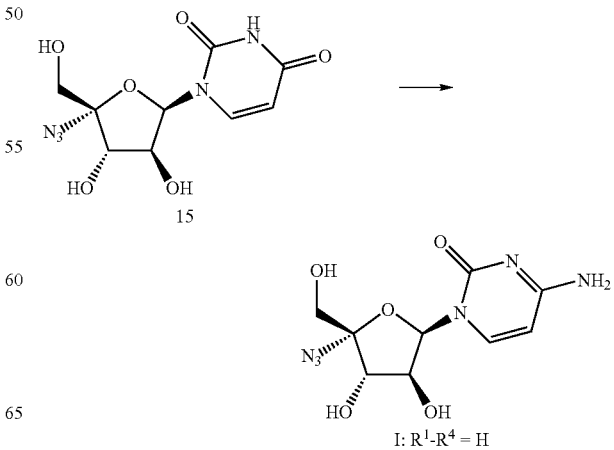

To a stirred solution of 4'-azido-arabino-uridine (15, 0.80 g, 2.84 mmol) in acetic anhydride (10 mL) and pyridine (10 mL) was added a trace of DMAP (catalytic) and the reaction mixture was stirred under $N_2$ at RT overnight. The volatile substances were evaporated to dryness under reduced pressure. To a solution of the resulting residue and MeCN (30 mL) was added triazole (3.09 g, 44.87 mmol) and TEA (7.81 mL, 56.09 mmol). The reaction mixture was flushed with $N_2$ and cooled to ~5° C. in an ice bath. $POCl_3$ (1.04 mL, 11.21 mmol) was added to the flask and the resulting mixture was left to stir at room temperature over night. The reaction mixture was evaporated to dryness under reduced pressure, dissolved in EtOAc (100 mL) and washed with saturated aqueous $NaHCO_3$, dried ($MgSO_4$) and evaporated to dryness to afford the protected triazole. $NH_4OH$ (2 mL) was added to a solution of the crude nucleoside in dioxane (5 mL). After stirring for 12 h the reaction mixture was evaporated to dryness. Preparative hplc chromatography (reverse phase ISCO column, $H_2O$/MeCN) provided 0.21 g, (26%) of I ($R^1$-$R^4$=H) as a white solid.

Example 3

Isobutyric acid (2R,3S,4S,5R)-5-(4-amino-2-oxo-2H-pyrimidin-1-yl)-2-azido-3,4-bis-isobutyryloxy-tetrahydro-furan-2-ylmethyl ester (I-2)

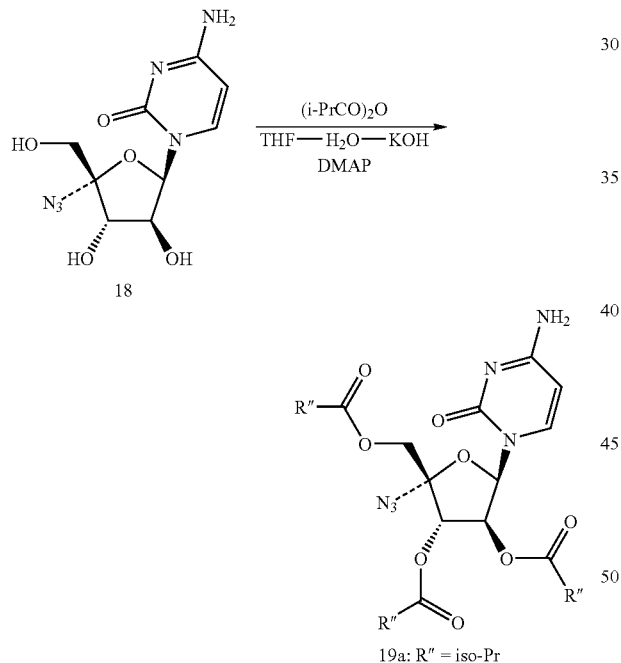

To a solution of 18 (2.0 g, 7.04 mmol), DMAP (0.09 g, 0.70 mmol), THF (12 mL) and water (8.0 mL) w added sufficient brine to cause the organic phase to separate (about 2 mL). The reaction mixture was cooled to about 5° C. and isobutyric anhydride was added dropwise. The pH of the reaction mixture was monitored during the addition and KOH (50% aqueous) was added as needed to maintain the pH at about 8.5. The reaction was complete after the addition of 3.56 g (22.52 mol) of the anhydride. The reaction mixture was diluted with EtOAc and organic phase was washed twice with brine. The combined aqueous phases were extracted with EtOAc (150 mL). The resulting EtOAc solution was washed with $H_2O$. The EtOAc solution was combined, dried ($Na_2SO_4$) and filtered. The organic solution was concentrated in vacuo, diluted with iso-propanol (about 10 mL) and methansulfonic acid (about 0.7 g). The solution was diluted with heptane (about 10 mL) and stirred at RT which produced a solid cake. A mixture of IPA/heptane (30 mL, 1:1) was added and the solution warmed to about 60° C. The resulting solution was allowed to cool to RT. The precipitate was filtered and washed with cold IPA/heptane (1:1), dried and transferred to a vacuum oven and heated to 60° C. for final drying which resulted in 3.35 g (80.5% theory) of 19a (R"=i-Pr): m.p. 167-169° C.

In similar fashion utilizing butyric anhydride in place of isobutyric anhydride there was obtained 1.45 g (83% theory) of 19a (R=n-$C_3H_7$) which was recrystallized from MTBE-heptane (m.p. 131-137° C.). Utilizing pentanoic anhydride in place of isobutyric anhydride there was obtained of 19a (R"=n-$C_4H_9$) which was recrystallized from MTBE-heptane (m.p. 145-146° C.).

Example 4

Pentanoic acid (2R,3S,4S,5R)-5-(4-amino-2-oxo-2H-pyrimidin-1-yl)-2-azido-2-hydroxymethyl-4-pentanoyloxy-tetrahydro-furan-3-yl ester (I-5)

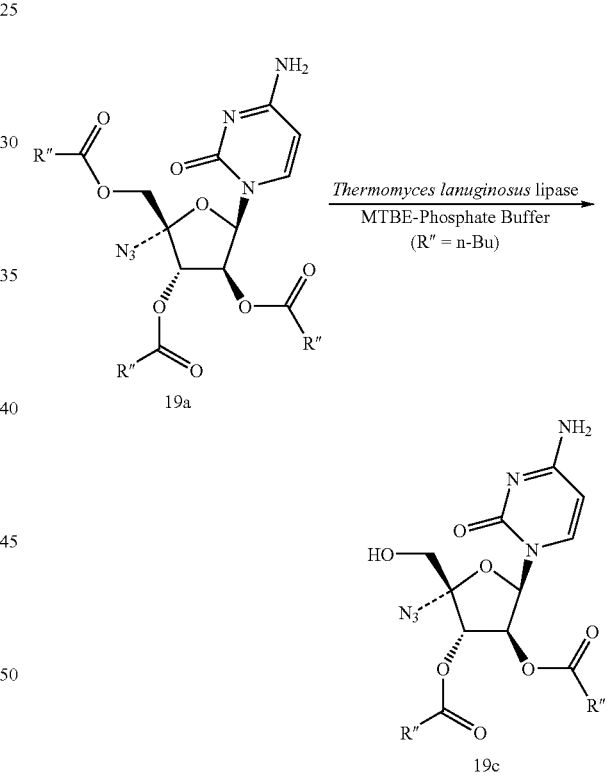

To a suspension of the tripentanoate ester 19a (R"=n-$C_4H_9$, 1.9 g, 3.46 mmol) in MTBE (13 mL) and phosphate buffer (15 mL, 5 mM sodium phosphate and 0.1 M NaCl adjusted to pH about 6.5) was added (about 2 mL) of Lipolase® (lipase from *Thermomyces Lanuginosus* Sigma catalog number L 0777). The reaction mixture was warmed to 35° C. and stirred for 2 h. The pH of the reaction mixture was maintained to 6.5 by the addition of $NaHCO_3$. After 2 h the reaction had proceeded to 8% completion. An additional 2 mL of Lipolase® was added and stirring was continued for 6 h whereupon an additional 2 mL aliquot of the enzyme was added and the reaction allowed to stir for an additional 24 h. To the solution was added acetone (10 mL), MTBE (20 mL) and brine (10 mL) and the reaction was warmed to 50° C. The phases were separated and the organic phase was twice extracted with warm MTBE. The combined organic phases were twice washed with hot brine, dried (Na₂SO₄), filtered and concentrated in vacuo. The resulting solid was redissolved in hot IPA (50 mL) and methanesulfonic acid (0.3 g) and heptane (50 mL) were added. The solution was warmed to 60° C. and allowed to slowly cool to RT. The resulting crystalline product was filtered and washed with IPA/heptane and dried in vacuo at 50° C. to afford 19c (R''=n-Bu): m.p. 160.4-162.2° C.

Example 5

Tetradecanoic acid (2R,3S,4S,5R)-5-(4-amino-2-oxo-2H-pyrimidin-1-yl)-2-azido-3,4-dihydroxy-tetrahydro-furan-2-ylmethyl ester (I-8)

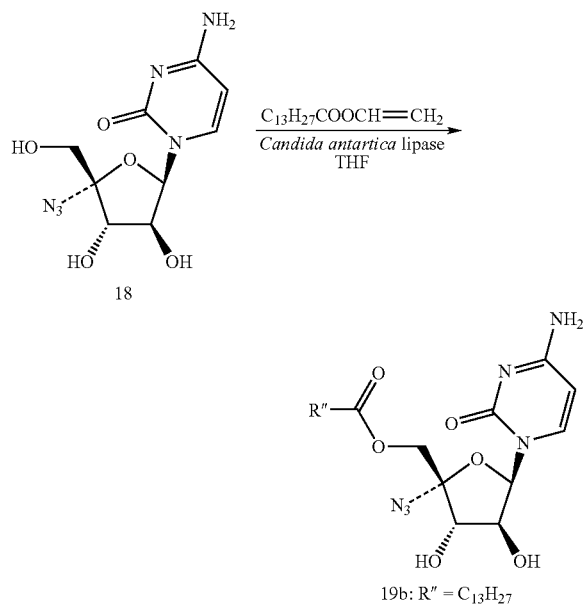

A suspension of 18 (1.0 g, 3.52 mmol), vinyl myristate (1.2 g, 4.57 mmol), *Candida antartica* lipase immobilized on polyacrylate resin (0.30 g; Sigma catalog no. L4777 from Novosome) and THF (20 mL) was warmed to 60° C. overnight. HPLC analysis indicated that the reaction was about 33% complete and an additional 2.4 of vinyl myristate and 0.3 g of lipase were added. After an additional 48 h the reaction was 50% complete and an additional 0.3 g of the enzyme and 3 mL of vinyl myristate were added. After approximately 80 h (total reaction time) conversion to the monoester appeared to be complete. The crude reaction mixture was filtered through CELITE® and the filter pad washed with THF. The combined organic phase was evaporated. The residue was dissolved in MeOH (50 mL) and extracted with hexane (2×20 mL). The methanolic solution was evaporated and the residue dissolved in EtOAc and washed with NaHCO₃ and the EtOAc phase dried (Na₂SO₄) filtered and evaporated to afford a 0.930 g of 19b (R''=C₁₃H₂₇) as a brown foam which was purified by chromatography on SiO₂ eluting with 5% MeOH/DCM and 10% MeOH/DCM and recrystallized the product from MeCN—H₂O): ms [M+H]⁺=495, mp=110.3-119.3° C.

Example 6

2-tert-Butoxycarbonylamino-3-methyl-butyric acid (2R,3S,4S,5R)-5-(4-amino-2-oxo-2H-pyrimidin-1-yl)-2-azido-3,4-dihydroxy-tetrahydro-furan-2-ylmethyl ester (1-7)

To a biphasic mixture of 17 (0.28 g, 1.00 mmol), DMAP (0.01 g, 0.1 mmol), THF (3 mL), water (3 mL) and brine (2 mL) was added 22 (0.29 g, 1.20 mmol) and THF (2 mL). To the stirred mixture was added 10% NaOH to maintain the pH at about 9.0. The reaction was monitored by HPLCn which indicated the formation of one monoester contaminated with small quantities of the other mono-, di- and tri-esters. The reaction mixture was partitioned between water and EtOAc and the EtOAc phase washed with brine, dried (Na₂SO₄), filtered and evaporated to afford 0.380 g of the crude 19b (R¹=BOC-Val) which was purified by SiO₂ column chromatography eluting with DCM/MeOH (19:1 to 14:1 to 12:1).

Example 7

*Renilla* Luciferase Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla* luciferase gene was introduced into the first open reading frame of a replicon construct NK5.1 (Krieger et al., *J. Virol.* 75:4614), immediately after the internal ribosome entry site (IRES) sequence, and fused with the neomycin phosphotransferase (NPTII) gene via a self-cleavage peptide 2A from foot and mouth disease virus (Ryan & Drew, EMBO Vol 13:928-933). After in vitro transcription the RNA was electroporated into human hepatoma Huh7 cells, and G418-resistant colonies were isolated and expanded. Stably selected cell line 2209-23 contain replicative HCV subgenomic RNA, and the activity of *Renilla* luciferase expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation. *Renilla* luciferase HCV replicon cells (2209-23) cultured in Dulbecco's MEM (GibcoBRL cat no. 31966-021) with 5% fetal calf serum (FCS, GibcoBRL cat. no. 10106-169) were plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using Dual-Luciferase reporter assay system (Promega cat no. E1960) All the reagents described in the following paragraph were included in the manufacturers kit, and the manufacturer's instructions were followed for preparations of the reagents. The cells were washed twice with 200 μl of phosphate buffered saline (pH 7.0) (PBS) per well and lysed with 25 μl of 1× passive lysis buffer prior to incubation at room temperature for 20 min. One hundred microlitre of LAR II reagent was added to each well. The plate was then inserted into the LB 96V microplate luminometer (MicroLumatPlus, Berthold), and 100 μl of Stop & Glo® reagent was injected into each well and the signal measured using a 2-second delay, 10-second measurement program. $IC_{50}$, the concentration of the drug required for reducing replicon level by 50% in relation to the untreated cell control value, can be calculated from the plot of percentage reduction of the luciferase activity vs. drug concentration.

WST-1 reagent from Roche Diagnostic (cat no. 1644807) was used for the cytotoxicity assay. Ten microlitre of WST-1 reagent was added to each well including wells that contain media alone as blanks.

Cells were then incubated for 1 to 1.5 hours at 37° C., and the OD value was measured by a 96-well plate reader at 450 nm (reference filter at 650 nm). Again $CC_{50}$, the concentration of the drug required for reducing cell proliferation by 50% in relation to the untreated cell control value, can be calculated from the plot of percentage reduction of the WST-1 value vs. drug concentration.

| Compound Number | Luciferase Activity $IC_{50}$ (μM) |
|---|---|
| I-1 | 0.22 |
| I-6 | 0.619 |

Example 8

Pharmaceutical compositions of the subject Compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

| Suppository Formulation (E) | |
| --- | --- |
| Ingredient | % wt./wt. |
| Active ingredient | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

We claim:

1. A compound of formula I

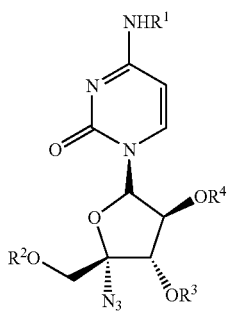

(I)

wherein:

$R^1$, $R^2$, $R^3$, and $R^4$ are independently selected from the group consisting of hydrogen, $COR^5$, $C(=O)OR^5$, $C(=O)SR^5$, $C(=O)NHR^5$ and $COCH(R^6)NHR^7$;

$R^5$ is independently selected from the group consisting of $C_{1-18}$ unbranched or branched alkyl, $C_{1-18}$ unbranched or branched alkenyl, $C_{1-18}$ unbranched or branched alkynyl, $C_{1-18}$ lower haloalkyl, $C_{3-8}$ cycloalkyl, $C_{3-8}$ cycloalkyl-$C_{1-3}$ alkyl, phenyl optionally substituted with one to three substituents independently selected from the group consisting of halo, $C_{1-6}$ alkyl, $C_{1-6}$ lower alkoxy, $C_{1-6}$ lower thioalkyl, $C_{1-6}$ lower alkyl sulfinyl, $C_{1-6}$ lower alkyl sulfonyl, nitro and cyano, $CH_2Ph$ wherein in phenyl ring is optionally substituted as described above, and $CH_2OPh$ wherein in phenyl ring is optionally substituted as described above;

$R^6$ is independently selected from the group consisting of the side chains of naturally occurring amino acids and $C_{1-5}$ unbranched or branched alkyl;

$R^7$ is selected from the group consisting of hydrogen and $R^5OCO$; or, $R^6$ and $R^7$ taken together are $(CH_2)_3$; and, acid addition salts thereof.

2. A compound according to claim 1 wherein $R^1$, $R^2$, $R^3$, and $R^4$ each are independently $COR^5$, $C(=O)OR^5$, $C(=O)SR^5$.

3. A compound according to claim 2 wherein $R^5$ is independently selected from the group consisting of unbranched or branched $C_{1-18}$ alkyl, optionally substituted phenyl and $CH_2OPh$.

4. A compound according to claim 1 wherein $R^1$ is hydrogen and $R^2$, $R^3$ and $R^4$ are independently $COR^5$, $C(=O)OR^5$, $C(=O)SR^5$ or $COCH(R^6)NHR^7$.

5. A compound according to claim 4 wherein $R^2$, $R^3$ and $R^4$ are independently $COR^5$.

6. A compound according to claim 5 wherein $R^5$ is selected from the group consisting of is $C_{1-18}$ unbranched or branched alkyl, $C_{3-8}$ cycloalkyl and optionally substituted phenyl.

7. A compound according to claim 1 wherein $R^2$ is selected from the group consisting of $COR^5$, $C(=O)OR^5$, $C(=O)SR^5$, and $COCH(R^6)NHR^7$, $R^1$, $R^3$ and $R^4$ are hydrogen.

8. A compound according to claim 7 wherein $R^2$ is $COR^5$.

9. A compound according to claim 8 wherein $R^5$ is selected from the group consisting of is $C_{1-18}$ unbranched or branched alkyl, $C_{3-8}$ cycloalkyl and optionally substituted phenyl.

10. A compound according to claim 1 wherein $R^1$ and $R^2$ are hydrogen and $R^3$ and $R^4$ are independently $COR^5$, $C(=O)OR^5$, $C(=O)SR^5$, or $COCH(R^6)NHR^7$.

11. A compound according to claim 10 wherein $R^3$ and $R^4$ are independently $COR^5$.

12. A compound according to claim 11 wherein $R^5$ is selected from the group consisting of is $C_{1-18}$ unbranched or branched alkyl, $C_{3-18}$ cycloalkyl and optionally substituted phenyl.

13. A method for treating Hepatitis C comprising administering to a mammal in need thereof, a therapeutically effective quantity of a compound according to claim 1.

14. The method of claim 13 wherein $R^1$ is hydrogen; $R^2$, $R^3$ and $R^4$ are each independently $COR^5$; and $R^5$ are independently selected from the group consisting of $C_{1-18}$ unbranched or branched lower alkyl, $C_{3-8}$ cycloalkyl, optionally substituted phenyl and $CH_2OPh$.

15. The method of claim 13 wherein $R^1$, $R^3$, and $R^4$ are hydrogen and $R^2$ is $COR^5$ and $R^5$ is independently selected from the group consisting of $C_{1-18}$ unbranched or branched lower alkyl, $C_{3-8}$ cycloalkyl, optionally substituted phenyl and $CH_2OPh$.

16. The method of claim 13 wherein $R^1$ and $R^2$ are hydrogen and $R^3$ and $R^2$ are independently $COR^5$ and $R^5$ is independently selected from the group consisting of $C_{1-8}$ unbranched or branched lower alkyl, $C_{3-8}$ cycloalkyl, optionally substituted phenyl and $CH_2OPh$.

17. The method of claim 13 wherein the compound is delivered in a dose of between 1 and 100 mg/kg of body weight of the patient per day.

18. The method of claim 13 further comprising administering at least one immune system modulator and/or at least one antiviral agent that inhibits replication of HCV.

19. The method of claim 13 wherein the immune system modulator is an interferon, interleukin, tumor necrosis factor or colony stimulating factor.

20. The method of claim 19 wherein the immune system modulator is an interferon or chemically derivatized interferon.

21. The method of claim 16 further comprising administering at least one other antiviral agent.

22. The method of claim 21 where the antiviral compound is selected from the group consisting of an HCV protease inhibitor, another nucleoside HCV polymerase inhibitor, a non-nucleoside HCV polymerase inhibitory, an HCV helicase inhibitor, an HCV primase inhibitor and an HCV fusion inhibitor.

23. A pharmaceutical composition comprising a therapeutically effective quantity of a compound according to claim 1 admixed with at least one pharmaceutically acceptable carrier, diluent, or excipient.

* * * * *